(12) United States Patent
Bishop et al.

(10) Patent No.: US 8,623,293 B2
(45) Date of Patent: Jan. 7, 2014

(54) SEALER FOR TEST SAMPLE DEVICES

(75) Inventors: James Clement Bishop, Columbia, MO (US); Michael J. Justin, St. Louis, MO (US); Mark Joseph Fanning, Florissant, MO (US)

(73) Assignee: Biomerieux, Inc., Durham, NC (US)

( * ) Notice: Subject to any disclaimer, the term of this patent is extended or adjusted under 35 U.S.C. 154(b) by 1055 days.

(21) Appl. No.: 12/228,782

(22) Filed: Aug. 14, 2008

(65) Prior Publication Data

US 2008/0314527 A1 Dec. 25, 2008

Related U.S. Application Data

(62) Division of application No. 10/695,517, filed on Oct. 28, 2003, now Pat. No. 7,429,355.

(51) Int. Cl.
*B01L 3/00* (2006.01)

(52) U.S. Cl.
USPC ............... 422/500; 422/105; 436/50; 436/55

(58) Field of Classification Search
USPC ..................................................... 422/50, 99
See application file for complete search history.

(56) References Cited

U.S. PATENT DOCUMENTS

| | | | | |
|---|---|---|---|---|
| 3,963,355 | A | 6/1976 | Aldridge, Jr. et al. | 435/39 |
| 4,038,151 | A | 7/1977 | Fadler et al. | 435/288.5 |
| 4,116,775 | A | 9/1978 | Charles et al. | 435/34 |
| 4,118,280 | A | 10/1978 | Charles et al. | 435/287.3 |
| 4,427,144 | A | 1/1984 | Macgrory et al. | 225/7 |
| 5,161,723 | A | 11/1992 | Wirtz-Odenthal | 225/14 |
| 5,471,016 | A | 11/1995 | Krainer et al. | 174/254 |
| 5,609,828 | A | 3/1997 | O'Bear et al. | 422/102 |
| D382,647 | S | 8/1997 | Staples et al. | D24/216 |
| 5,670,375 | A | 9/1997 | Seaton et al. | 436/48 |
| 5,736,102 | A | 4/1998 | Seaton et al. | 422/65 |
| 5,746,980 | A | 5/1998 | O'Bear et al. | 422/102 |
| 5,762,873 | A | 6/1998 | Fanning et al. | 422/65 |
| 5,762,874 | A | 6/1998 | Seaton et al. | 422/65 |
| 5,766,553 | A | 6/1998 | Staples et al. | 422/102 |
| 5,798,084 | A | 8/1998 | Seaton et al. | 422/65 |
| 5,798,085 | A | 8/1998 | Seaton et al. | 422/65 |
| 5,798,182 | A | 8/1998 | LeFebvre et al. | 428/428 |
| 5,804,437 | A | 9/1998 | Tegeler et al. | 435/287.1 |
| 5,843,380 | A | 12/1998 | Staples et al. | 422/102 |
| 5,853,666 | A | 12/1998 | Seaton et al. | 422/65 |
| 5,853,667 | A | 12/1998 | Seaton et al. | 422/65 |

(Continued)

FOREIGN PATENT DOCUMENTS

DE 3049840 4/1987 ............ B65H 35/07

*Primary Examiner* — Natalia Levkovich
(74) *Attorney, Agent, or Firm* — McDonnell Boehnen Hulbert & Berghoff LLP

(57) ABSTRACT

A sealer for a sample testing instrument is disclosed that cuts and seals a fluid conduit that connects a test sample device with a fluid receptacle containing a fluid sample. The sealer includes an enclosure and a protective shield to protect a user or technician from contact with the cutting element assembly in the sealer. The cutting element assembly includes a spring-loaded element that engages the test sample device and holds it in a fixed position while a cutting element (e.g., hot wire) cuts the fluid conduit. A motor driving the cutting element assembly is positioned at an angle having both vertical and horizontal components, whereby adjustment of the motor firmware allows for adjustment of the position of the cutting element relative to the instrument in both horizontal and vertical directions.

7 Claims, 33 Drawing Sheets

(56) References Cited

U.S. PATENT DOCUMENTS

| | | | |
|---|---|---|---|
| 5,869,005 A | 2/1999 | O'Bear et al. | 422/67 |
| 5,869,006 A | 2/1999 | Fanning et al. | 422/67 |
| 5,888,455 A | 3/1999 | Seaton et al. | 422/65 |
| 5,891,396 A * | 4/1999 | Karl et al. | 422/65 |
| 5,897,835 A | 4/1999 | Seaton et al. | 422/104 |
| 5,916,812 A | 6/1999 | Chen et al. | 436/18 |
| 5,925,884 A | 7/1999 | Robinson et al. | 250/458.1 |
| 5,932,177 A | 8/1999 | O'Bear et al. | 422/102 |
| D414,272 S | 9/1999 | O'Bear et al. | D24/255 |
| 5,951,952 A | 9/1999 | O'Bear et al. | 422/102 |
| 5,965,090 A | 10/1999 | Fanning et al. | 422/65 |
| 6,024,921 A | 2/2000 | Freiner et al. | 422/66 |
| 6,045,758 A | 4/2000 | Staples et al. | 422/102 |
| 6,086,824 A | 7/2000 | Fanning et al. | 422/65 |
| 6,136,270 A | 10/2000 | Maes et al. | 422/64 |
| 6,156,565 A | 12/2000 | Maes et al. | 435/287.3 |
| 6,309,890 B1 | 10/2001 | Tegeler et al. | 436/180 |

\* cited by examiner

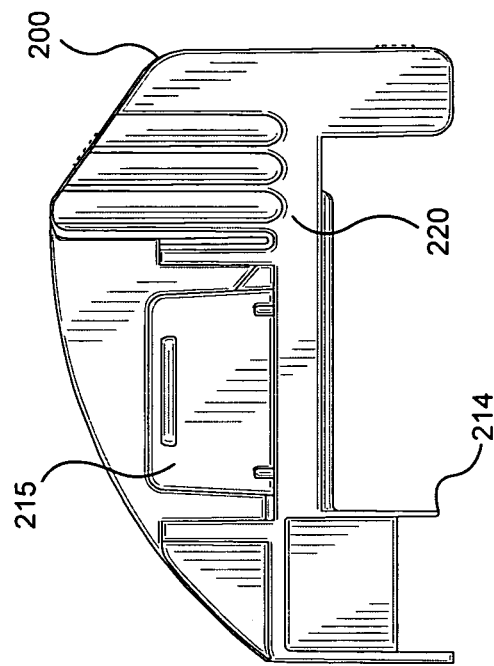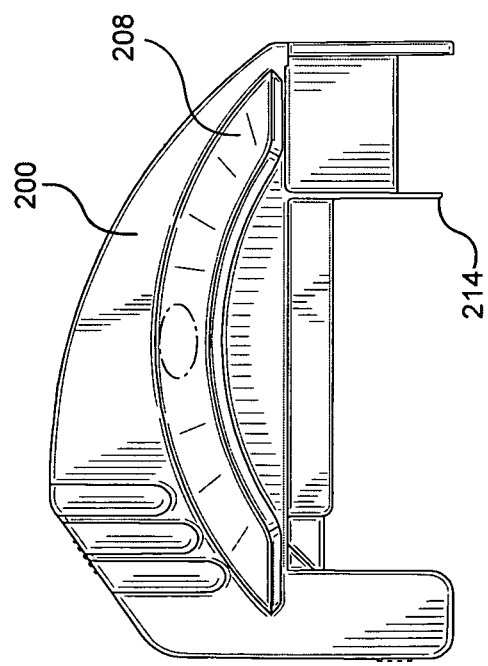

SEALER FOR TEST SAMPLE DEVICES

CROSS-REFERENCE TO RELATED APPLICATIONS

This is a divisional of U.S. patent application Ser. No. 10/695,517 filed Oct. 28, 2003, allowed.

BACKGROUND OF THE INVENTION

1. Field of the Invention

This invention relates to devices and related instruments and systems that test biological, microbiological, chemical or other types of samples. The invention in particular relates to a sealer assembly for sealing test sample devices that are supplied with a fluid sample via a transfer tube.

2. Description of Related Art

Biological samples can be reacted and subjected to chemical or optical analysis using various techniques, including transmittance and/or fluorescence optical analysis. The purpose of the analysis may be to identify an unknown biological agent or target in the sample, to determine the concentration of a substance in the sample, or determine whether the biological agent is susceptible to certain antibiotics, as well as the concentration of antibiotics that would be effective in treating an infection caused by the agent.

In the mid-to late 1970's, engineers and scientists working with the applicants' assignee and its predecessor in interest developed a technique for conducting optical analysis of biological samples using a sealed test sample card containing a plurality of small sample wells. The technique, and related instruments and devices, came to be known in the industry as the "Vitek® System". The Vitek® System was (and continues to be) a commercial success.

The cards used in the Vitek System are known in the patent literature, see e.g., U.S. Pat. Nos. 4,118,280, 3,963,355, 4,018,65; 4,116,775 and 4,038,151. More recent versions of the cards are described in U.S. Pat. Nos. Des. 382,647, Des. 414,272, 5,609,828, 5,746,980, 5,766,553, 5,843,380, 5,869,005, 5,916,812, 5,932,177, 5,951,952, and 6,045,758.

Cards were developed for both identification of unknown microorganisms that may be present in a sample and susceptibility of a known organism to precisely calibrated concentrations of antibiotics. During manufacture of the cards, the wells are filled with either various types of growth media for various biological agents, or else concentrations of different antibiotics, and covered with a transparent sealing tape.

The cards have an external transfer tube port as a mechanism for allowing a fluid sample to enter the card. The cards further include an internal fluid passageway structure for allowing fluid to enter the wells of the card from the transfer tube port. One end of straw-like transfer tube is inserted into the transfer tube port. The other end is inserted into an open receptacle (e.g., test tube) containing the fluid sample to be tested. In accordance with the teaching of the prior art Charles et al. U.S. Pat. No. 4,188,280, the card with attached transfer tube and test tube are placed into a stand-alone vacuum and filling sealing machine, known as the Vitek® Filler Sealer. The filling and sealing machine generates a vacuum. When the vacuum is released, the fluid sample is drawn from the test tube into the transfer tube and through the internal channels of the card and into all of the sample wells. In the instrument of the prior art Charles et al. '280 patent, after the wells of the card are loaded with the sample, the cards are manually inserted into a slot in a sealer module in the machine, where the transfer tube is cut and melted, sealing the interior of the card.

The cards are then manually removed from the filler/sealer module and loaded into a reading and incubating machine, known as the VITEK® Reader, also described in the Charles et al. '280 patent. The reading and incubating machine incubates the cards at a desired temperature. An optical reader is provided for conducting transmittance testing of the wells of the card. Basically, the cards are stacked in columns in the reading machine, and an optical system moves up and down the column of cards, pulling the cards into the transmittance optics one at a time, reading the cards, and placing the cards back in the column of cards.

The arrangement of the early Vitek System (as described in the Charles et al. '280 patent) has several limitations, in that two machines, a filler/sealer and a reader, are required to process and analyze the cards. Furthermore, additional time and labor are required to conduct the complete analysis of the card. The applicants' assignee later developed and commercialized a fully automated instrument, referred to herein and known in the art as the "Vitek 2" instrument. The Vitek 2 instrument automates both the vacuum loading and sealing operations and combined them with incubation and reading in a single instrument.

Briefly, the "Vitek 2" system provides an automated sample testing machine that performs dilutions for susceptibility testing, fills the cards with the samples at a vacuum station, and seals the card by cutting the transfer tube, and conducts incubation and optical transmittance and fluorescence analysis of the cards, all automatically. The machine provides for novel pipetting and diluting stations, permitting fluids to be added to the test tubes or transferred from one test tube to another. The machine is capable of conducting simultaneous susceptibility and identification testing of a sample placed in a single test tube. The machine provides for rapid, automatic identification and susceptibility testing of the sample.

The instrument uses a sample tray or "boat" and a test sample positioning or transportation system that moves the "boat" in four separate paths around a rectangular base pan among the various stations. The user places a cassette loaded with cards and test tubes containing samples into the boat at a loading station. The design of the positioning system is such that it permits essentially a custom configuration of stations above the base pan. Expansion of the machine to include additional carousels and reading stations, or addition types in intermediate procession stations such as dilution stations or vacuum stations, can be readily accomplished.

The overall instrument is described in several patents, including U.S. Pat. Nos. 5,762,873 and 6,086,824, the contents of which are incorporated by reference herein. The cutting and sealing station that cuts the transfer tubes to seal the cards is described in U.S. Pat. No. 5,891,396, particularly in FIGS. 1, 4 and 5 thereof and at columns 15 and 16 thereof. The entire content of the above-listed patents is incorporated by reference herein.

Various aspects of the present invention provide an improvement to the sealing arrangement described in U.S. Pat. No. 5,891,396. In particular, the present arrangements provide for easier and more accurate alignment of the sealer to the test devices and transfer tubes, a pre-loading feature that allows for cutting of the transfer tubes with tighter tolerances, and safety features that prevent inadvertent touching of the hot cutting wire.

SUMMARY OF THE INVENTION

In a first aspect, a safety feature is provided for a sealer that involves the design of an enclosure for the sealer and a retractable shield that prevents inadvertent user contact with the cutting assembly. In particular, a sealer for cutting and sealing a conduit connecting a test sample device to a fluid receptacle containing a fluid sample is provided. The sealer includes an enclosure having an aperture and shield moveable between a first position covering the aperture and a second, retracted position. The sealer includes a moveable cutting element assembly (e.g., heated wire and associated structures) that has a home position located within enclosure. The sealer further includes a motor for moving the cutting element assembly through the aperture to a deployed position, in which the cutting element assembly is positioned external to the enclosure at a position for cutting the conduit. The action of movement of the cutting element assembly through the aperture causes the shield to move to the retracted position. Furthermore, the action of movement of the cutting assembly from the deployed position to the home position causes the shield to retract to the first position covering the aperture. Accordingly, when the cutting element is in the home position the shield and the enclosure prevent inadvertent contact with the cutting assembly.

In a second aspect, a sealer is designed such that the cutting of the fluid conduit (transfer tube) is controlled more precisely. This is achieved by a spring loaded member or "shoe" and corresponding fixed structure in the instrument that, together, hold the test sample device in position and prevent lateral movement while the cutting element cuts through the transfer tube. In this embodiment, the sealer is installed in an automated sample testing instrument. The moveable cutting element assembly has a home position and a deployed position. The cutting element assembly comprises a cutting wire and the spring-loaded member or "shoe". The shoe engages with the test sample device when the cutting element assembly is moved to the deployed position. The sealer further includes a motor for moving the cutting element assembly from the home position to the deployed position. Operation of the shoe is such that when the cutting element assembly is moved to the deployed position, the engagement of the shoe with the test sample device urges the test sample device against the fixed structure in the instrument (e.g., horizontally extending rail) to thereby hold the test sample device while the cutting wire cuts and seals the conduit. The fixed structure can be any suitable structure (surface, rail, or specially designed structure), that is positioned relative to the sealer such that when the sealer's cutting element is in the deployed position, the spring loaded member engages the test sample device and hold the device, i.e., prevent lateral movement, while the cutting wire cuts the conduit. The cutting action may occur by movement of the test device past the wire, in which case the spring loaded member permits the motion of the test device past the wire in the direction of travel but still holds the device against the fixed structure to prevent substantial lateral movement (movement perpendicular to the direction of travel of the test sample device past the wire).

In another aspect, the positioning of the cutting assembly relative to the test sample device and the conduit to be cut and sealed is more closely by means of a unique arrangement in which a single motor moves the cutting assembly in a direction having both vertical and horizontal components (i.e., at an angle). Changing the operation of the motor (such as by adjusting the motor firmware to set limits on motor travel), adjusts the position of the cutting element assembly in both the horizontal and vertical directions. In particular, a sealer for cutting and thereby sealing a conduit connecting a test sample device to a fluid receptacle containing a fluid sample is provided. The sealer is installed in an automated sample-testing instrument. The sealer includes the moveable cutting element assembly and the motor for moving the cutting element assembly from the home position to the deployed position. The motor is constructed and arranged such that the motor drives the cutting element assembly relative to the enclosure in a direction having both vertical and horizontal components relative to the instrument, whereby adjustment of the operation of the motor results in adjustment of the position of the cutting element assembly relative to the instrument in both horizontal and vertical directions.

These and other features of the sealer arrangements will be more fully appreciated after consideration of the following detailed description and the appended drawing figures.

BRIEF DESCRIPTION OF THE DRAWINGS

FIG. 13 is an end view of the carrier of FIG. 7, showing the handle.

FIG. 14 is an opposite end view of the carrier of FIG. 7.

DETAILED DESCRIPTION OF PREFERRED EMBODIMENT

The present invention relates to a sealing mechanism for sealing a transfer tube or like structure in a test sample device. A presently preferred embodiment of a sealer station 400 in an automated sample testing instrument 10 is described in conjunction with FIGS. 7, 17, 18, and 22-24. In order to appreciate how the illustrated embodiment of the sealer invention operates, the specification will describe the invention in the context of a particular sample testing instrument and test sample device format. However, the invention can be practiced in other environments and the present description is provided by way of illustration and not limitation.

System Overview

An overview of a compact, high throughput instrument for processing test samples will now be described in conjunction with FIGS. 1-5. The details on the construction and operation of the instrument will be described later in conjunction with FIGS. 6-34.

Figure 6:
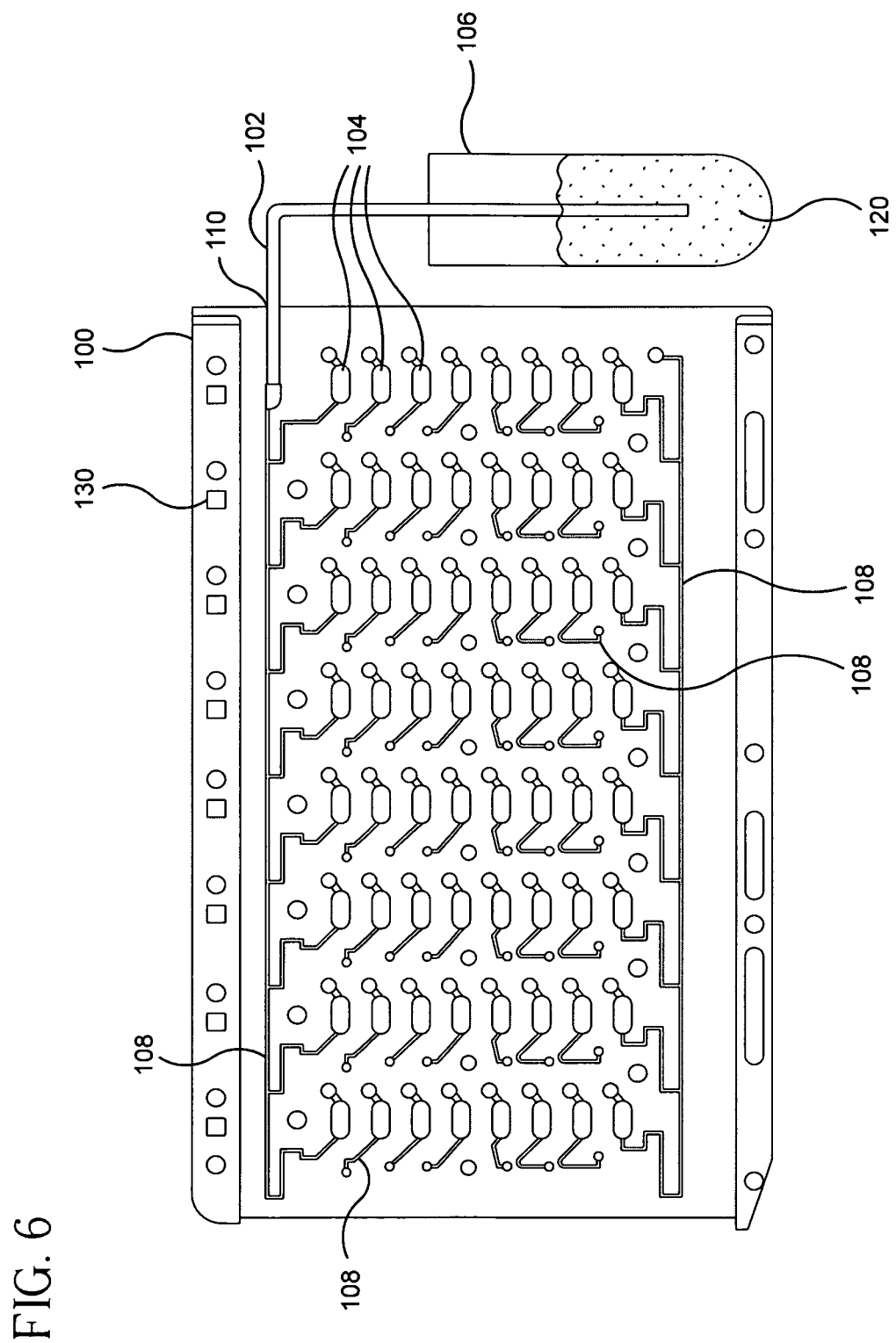
FIG. 6 is an elevational view of a test sample device in the form of a multi-well test sample card. The instrument of FIGS. 1-5 is designed to process a batch of cards of FIG. 6 at a time by means of a carrier. The carrier receives a plurality of the test sample cards of FIG. 6 and a plurality of open receptacles, e.g., test tubes, containing a fluid sample to be tested.

The instrument 10 processes a batch of test sample devices in the form of multi-well test sample cards in the illustrated embodiment. A representative test sample card 100 is shown in FIG. 6 and will be described subsequently. The cards 100 are initially loaded in a cassette (carrier) 200 shown in FIGS. 7-15. The carrier 200 further carries a set of fluid receptacles (test tubes) 106 (FIG. 7) that contain a fluid sample. Each test sample device 100 is placed into fluid communication with an associated fluid receptacle 106 by means of a transfer tube 102, shown in FIGS. 6 and 7. The sample is loaded into the card by means of a vacuum loading station in the instrument 10 in the manner described below.

The instrument 10 of FIGS. 1-5 is a sample processing and data collection portion of an overall sample testing system. The overall system includes a separate stand-alone identification station where bar codes on the test sample devices are scanned, the cards are loaded into the carrier 200, and the carrier is applied with a bar code and scanned. These functions are similar to the separate identification system described in the patent of Fanning et al., U.S. Pat. No. 5,869, 006, incorporated by reference herein. The overall system further includes a workstation having a computer processing system that receives data from the reading system in the instrument. These identification and computer processing aspects of the overall system are not particularly pertinent to the present invention and only insofar as they are relevant will they be discussed further.

The illustrated instrument was designed as a smaller and lower-cost alternative to more complex sample testing instruments, such as the system described in the above-referenced Fanning et al. patent, for use in low to medium range applications in both the clinical and industry markets. The instrument provides for semi-automated filling, sealing, and loading of the test sample devices, as will be described in detail below. However, whereas the prior art Fanning et al. '006 patent and the Vitek 2 instrument supported automated diluting and pipetting functions, these functions are performed off-line by the user either manually or using other equipment. In other words, the user prepares the samples so that they can be directly loaded into the test sample devices from their associated test tube. These off-line tasks will be discussed in more detail in conjunction with the work flow chart of FIG. 34.

As in the case with the Vitek 2 instrument, the instrument 10 of FIG. 1-5 provides a vacuum station 300 for inoculation of the fluid samples into the wells 104 of the test sample card 100 FIG. 6. However, in the present system the vacuum loading is performed semi-automatically as described herein, not fully automatically. In particular, the user manually places the loaded carrier into the vacuum station. When the fluid samples enter the wells 104 of the card 100, the fluid sample rehydrates reagents previously loaded into the wells of the card at the time of manufacture.

After vacuum loading, the carrier 200 is then manually placed into a separate compartment in the instrument 10 containing a carrier and test sample device processing subsystem 50. This subsystem 50 includes a sealing station 400 which operates to seal the cards by cutting the fluid transfer tube 102. The instrument 10 includes a card autoloader subsystem 500 that automatically loads the cards 100 one at a time into an incubation station 600. The incubation station 600 includes a rotating carousel that holds the cards. The cards are held at a precisely controlled temperature. The incubation system includes a card eject mechanism that ejects the cards from the carousel one at a time and places the cards on a transport assembly 700 that carries the cards to a card reader subsystem 800. The card reader subsystem 800 includes transmittance optics stations that perform periodic colorimetric readings of the wells 104 of the cards 100. A software algorithm determines changes in patterns of individual reagent wells 104 and translates those patterns into organism identification or sets of antimicrobial results. When the reading is deemed complete, the cards 100 are sent by the card transport assembly 700 to a card disposal system 900, which holds the cards for removal from the instrument by the user. If further reading is required, the cards are moved back into the incubation station 600 for further incubation and additional reading.

A carrier transport system 1000 is provided in the instrument for moving the loaded carrier 200 back and forth within the interior of the carrier and test sample device processing subsystem 50 of the instrument 10. The transport assembly 1000 is described in conjunction with FIGS. 29-33.

The instrument of FIGS. 1-5 and 16-33 can be scaled up or down to offer capacity for processing 60 test sample cards at the same time, or even more. The present discussion will focus on an embodiment for processing six fully loaded carriers (60 test sample devices). It will be appreciated that by providing a larger carousel incubation station or a second incubation station and second optics station and associated card transport assemblies the capacity could double.

The instrument 10 performs all control of sample well (test sample card) filling and incubation/optical reading. The instrument 10 also supports a two-step user workflow for test pre-processing: reagent hydration and sample inoculation (vacuum loading). The test pre-processing is followed by the steps performed automatically in the instrument: cassette and test setup verification using strategically placed bar code reader in the instrument, card transfer tube sealing, loading of test sample cards into the incubation station, reading of the cards, and unloading and return to the user of the processed carrier and test tubes. Upon loading of the cards 100 into the incubation system 600, the instrument controls incubation temperature, optical reading, and data transfer to the workstation computer processing system during the test processing period. The instrument then ejects the cards upon test finalization, by means of transport of the test sample cards into the card disposal system 900.

Door and User Interface Features (FIGS. 1-3B)

Figure 3:
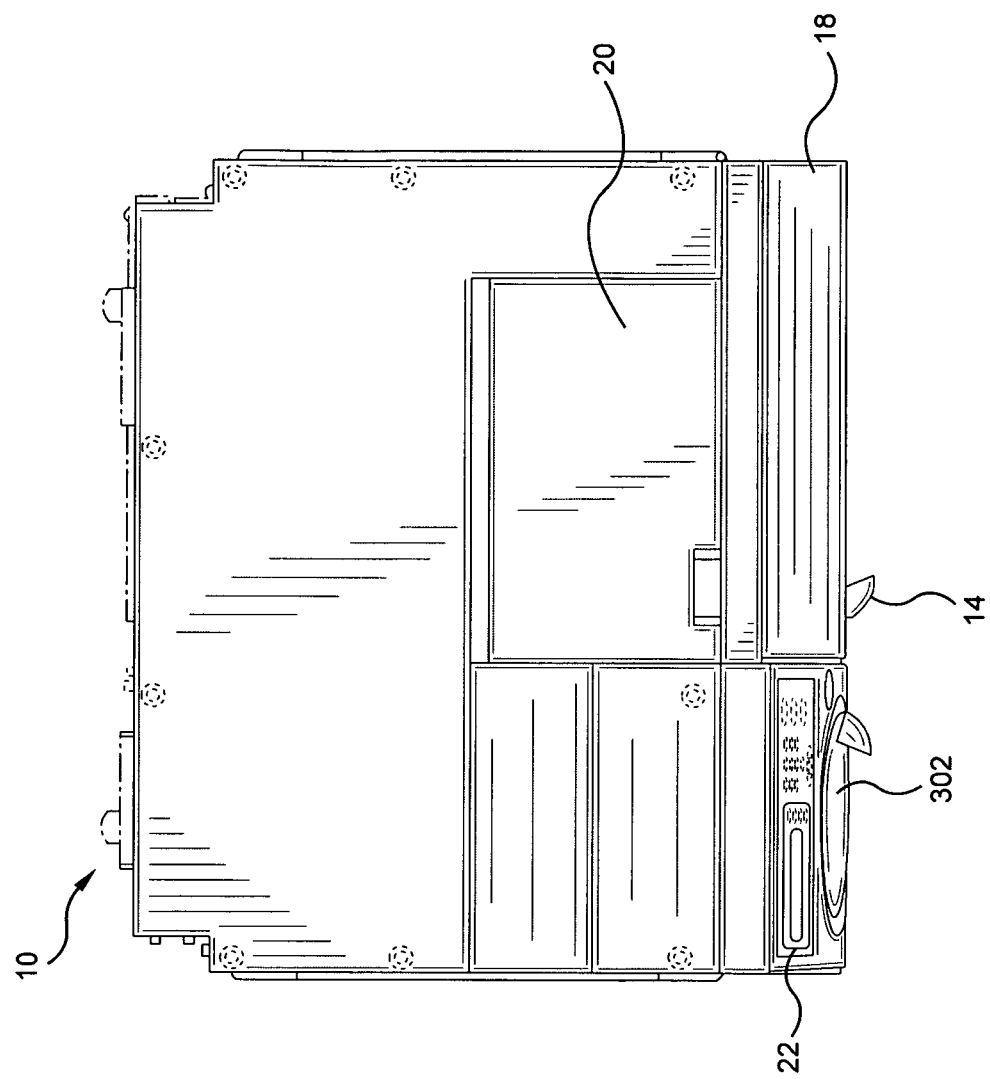
FIG. 3 is a top view of the instrument of FIG. 1.
Figure 3A:
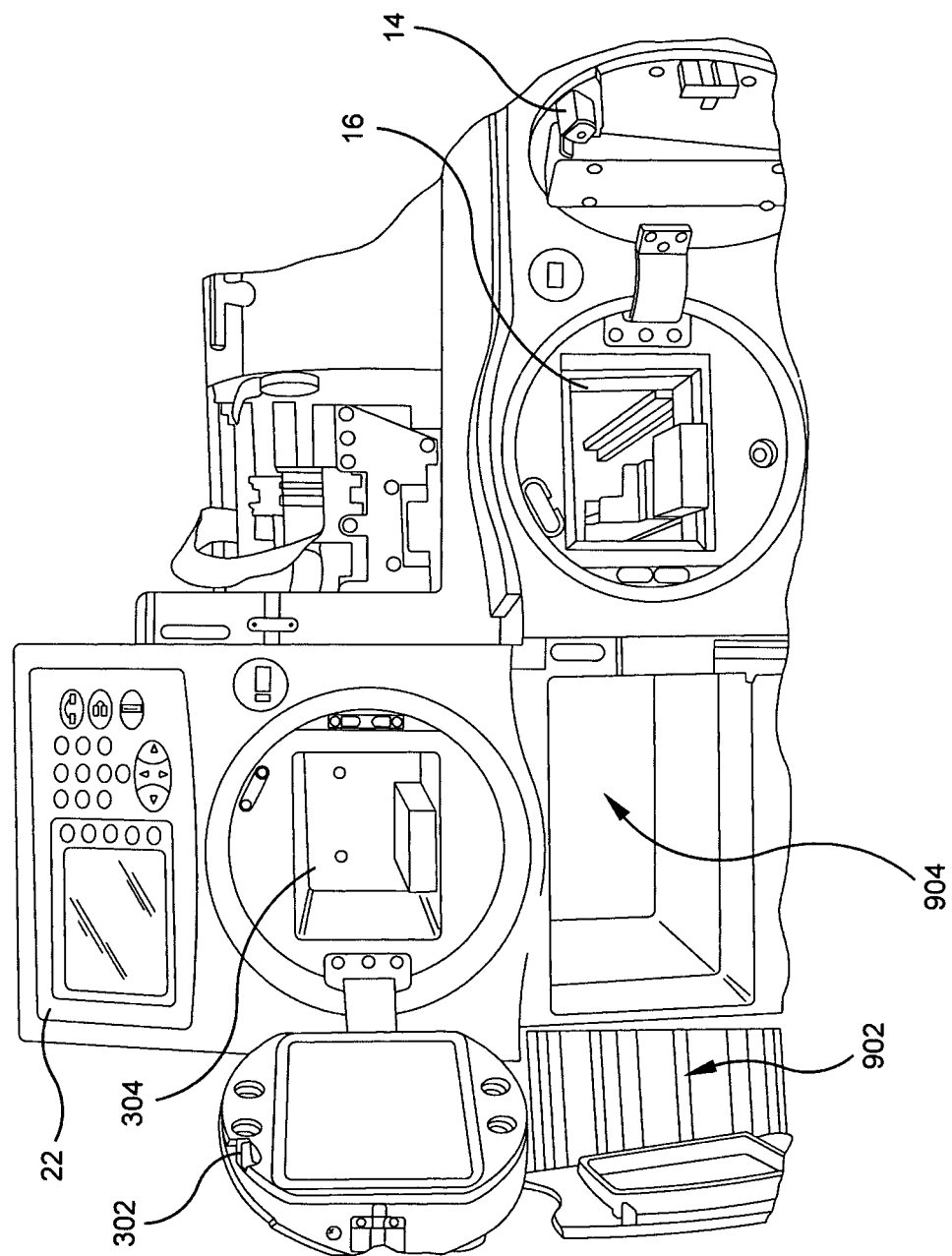
FIG. 3A is a front view of the instrument of FIG. 1 with the front doors and panels open and the top panel and user access, removed.
Figure 3B:
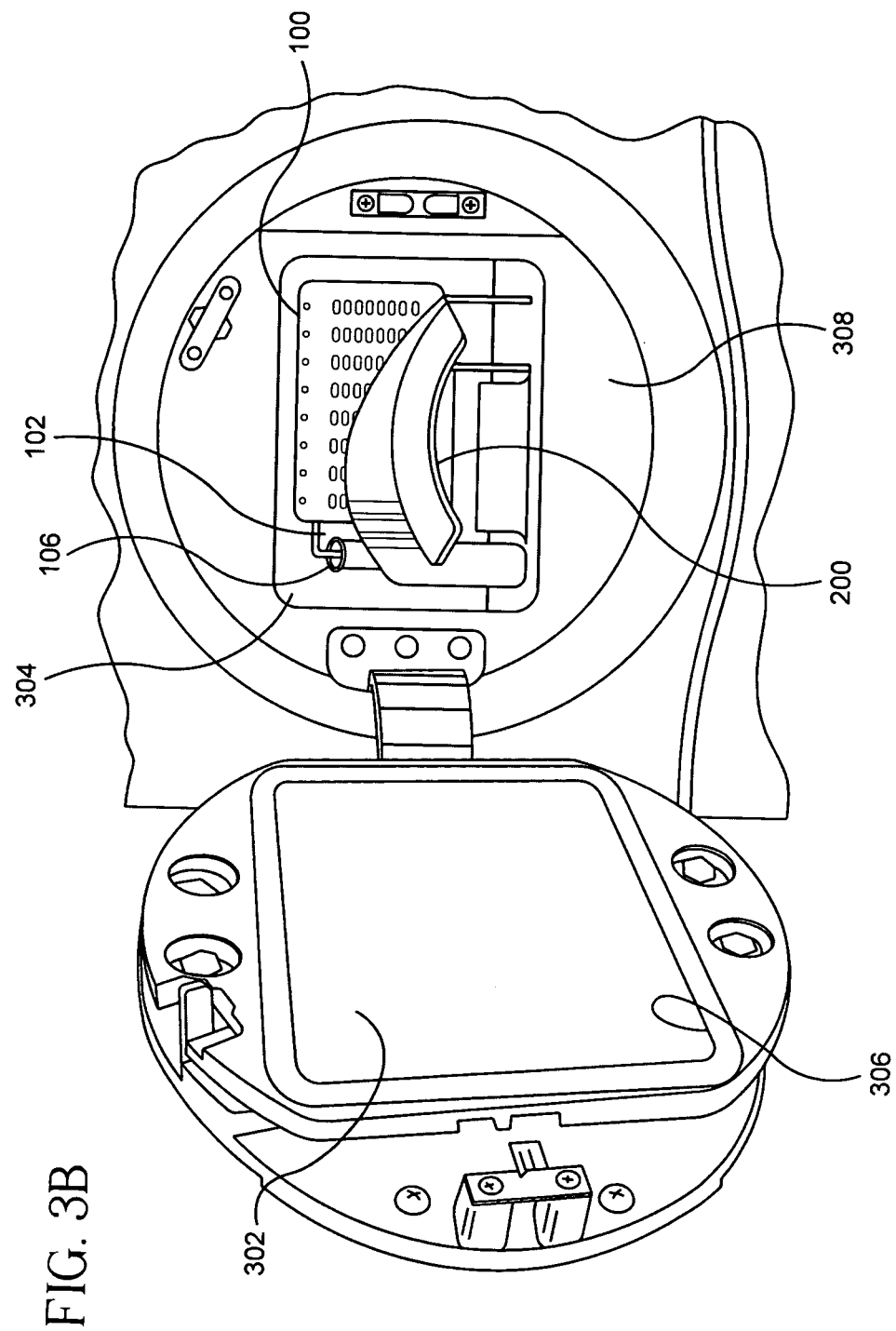
FIG. 3B is a detailed front view of the vacuum chamber with the door open showing placement of a loaded carrier with test sample devices and test tubes positioned within the vacuum chamber.
Figure 4:
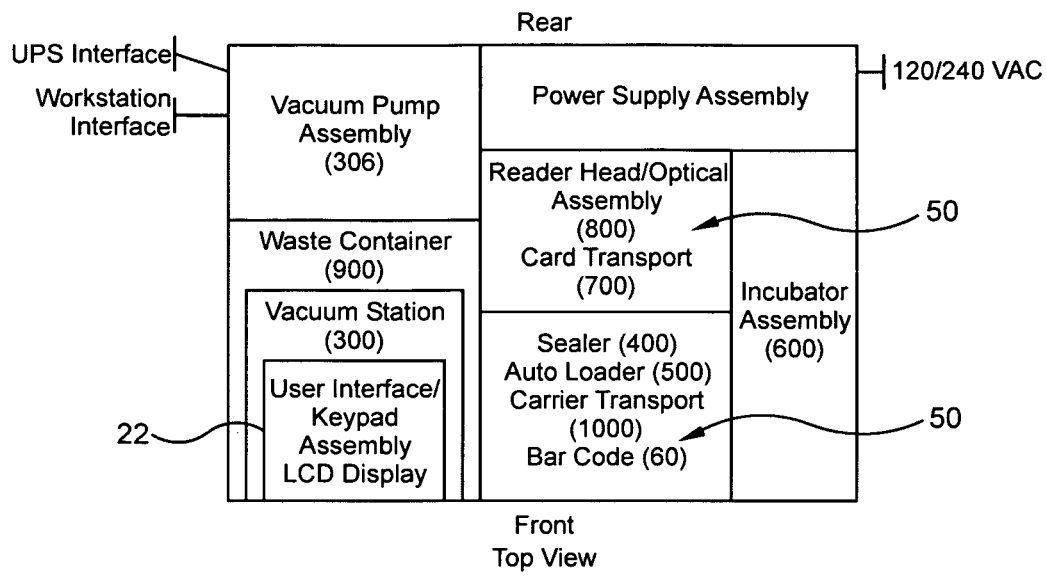
FIGS. 4 and 5 are diagrams of top and front views, respectively, of the instrument of FIG. 1, showing the general location of specific sub-assemblies and sub-systems in the instrument; familiarity with these figures will be helpful in understanding the more detailed drawings in the subsequent figures, particularly FIGS. 16-21.
Figure 5:
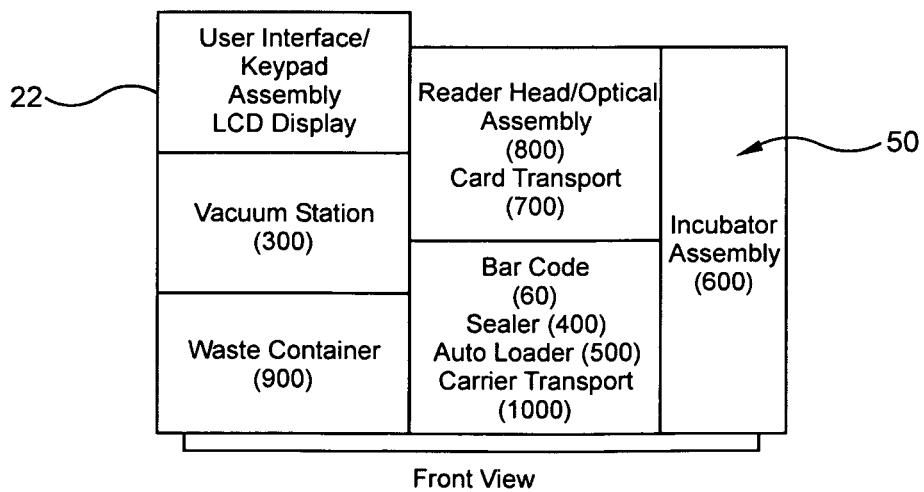
Figure 7:
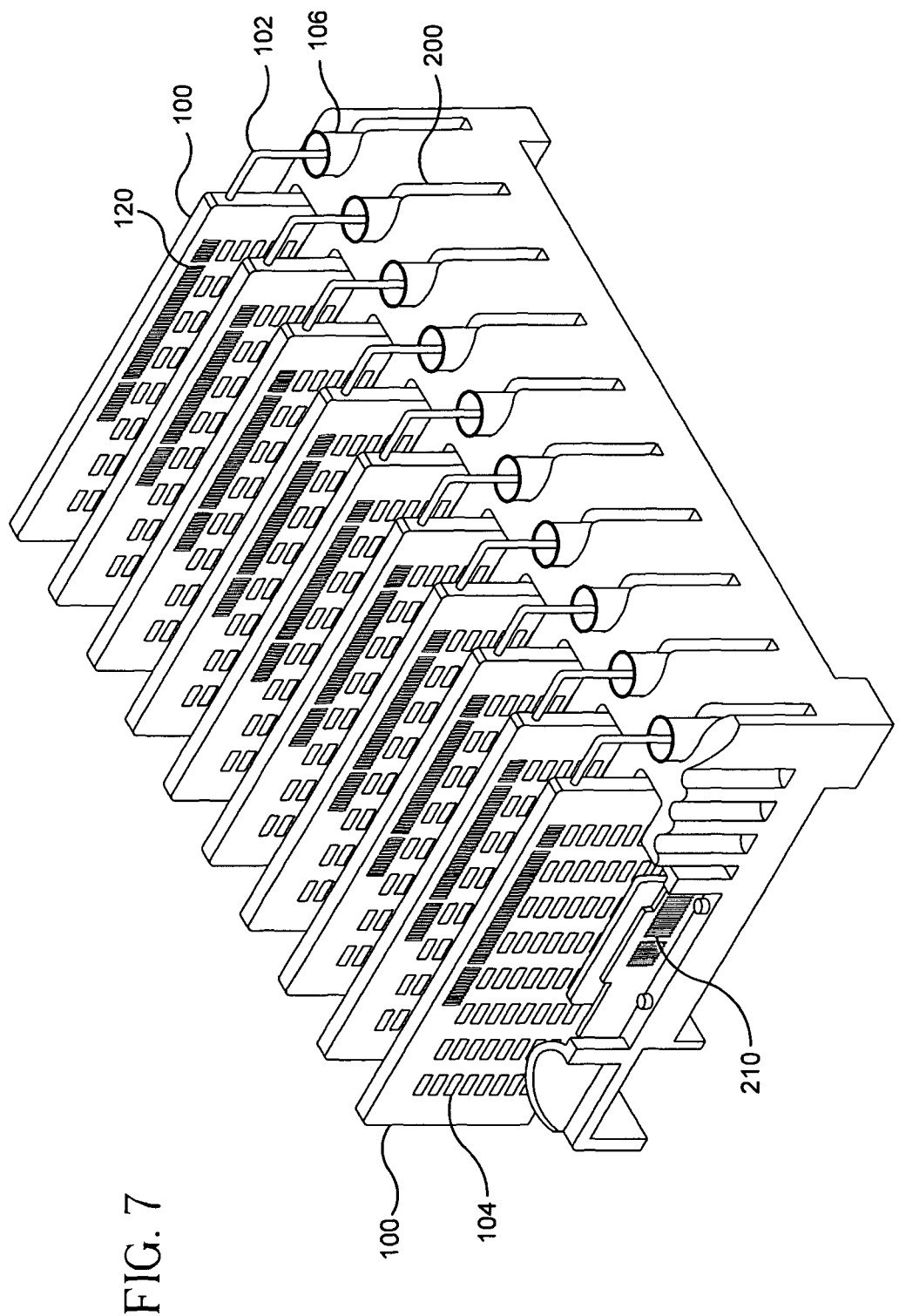
FIG. 7 is a perspective view of a carrier loaded with test sample devices and open receptacles. When the test sample devices and receptacles are placed in the carrier, each of the test sample devices is placed in fluid communication with a sample in an open receptacle by means of a transfer tube, as shown.
Figure 8:
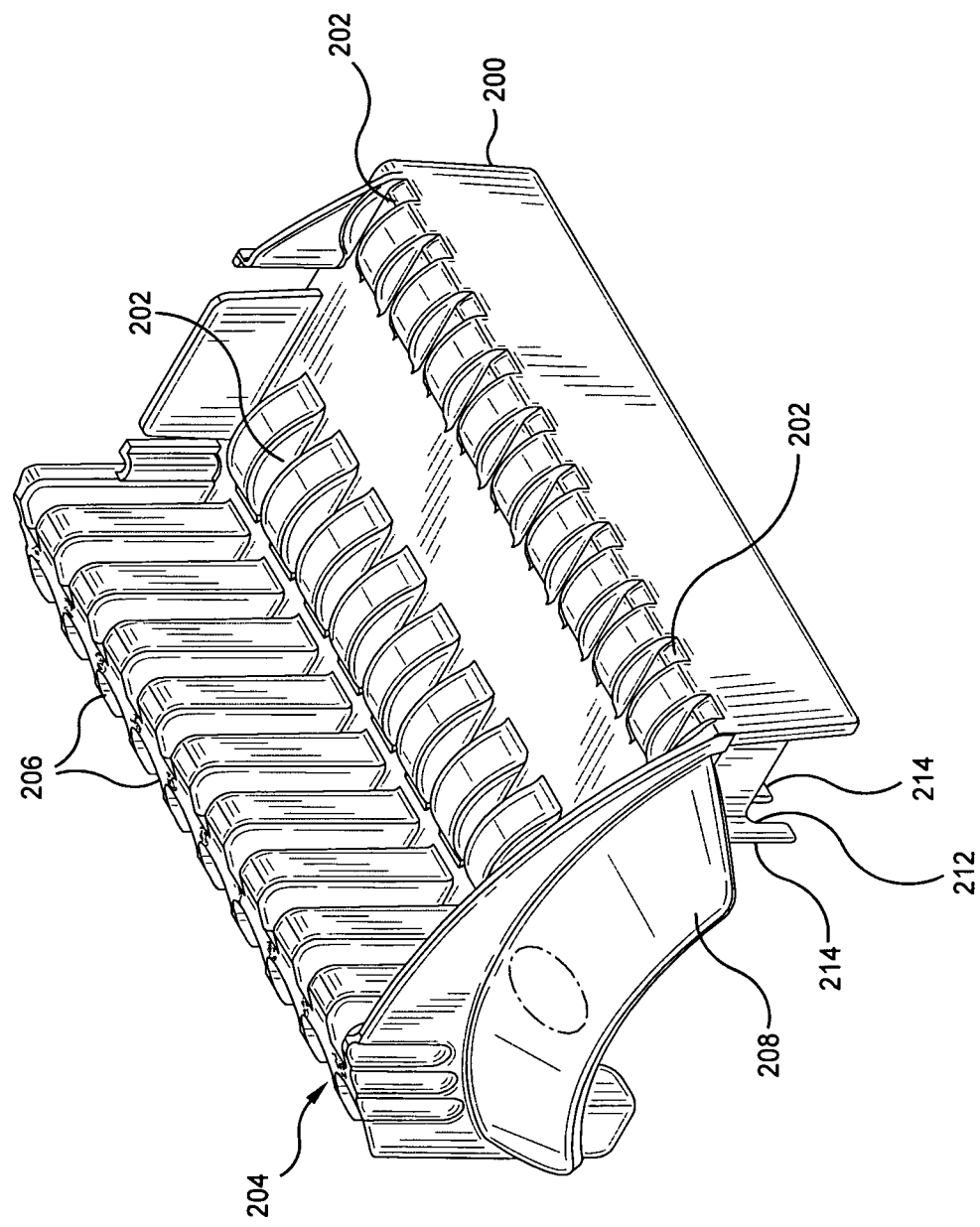
FIG. 8 is a perspective view of an empty carrier of FIG. 7.
Figure 9:
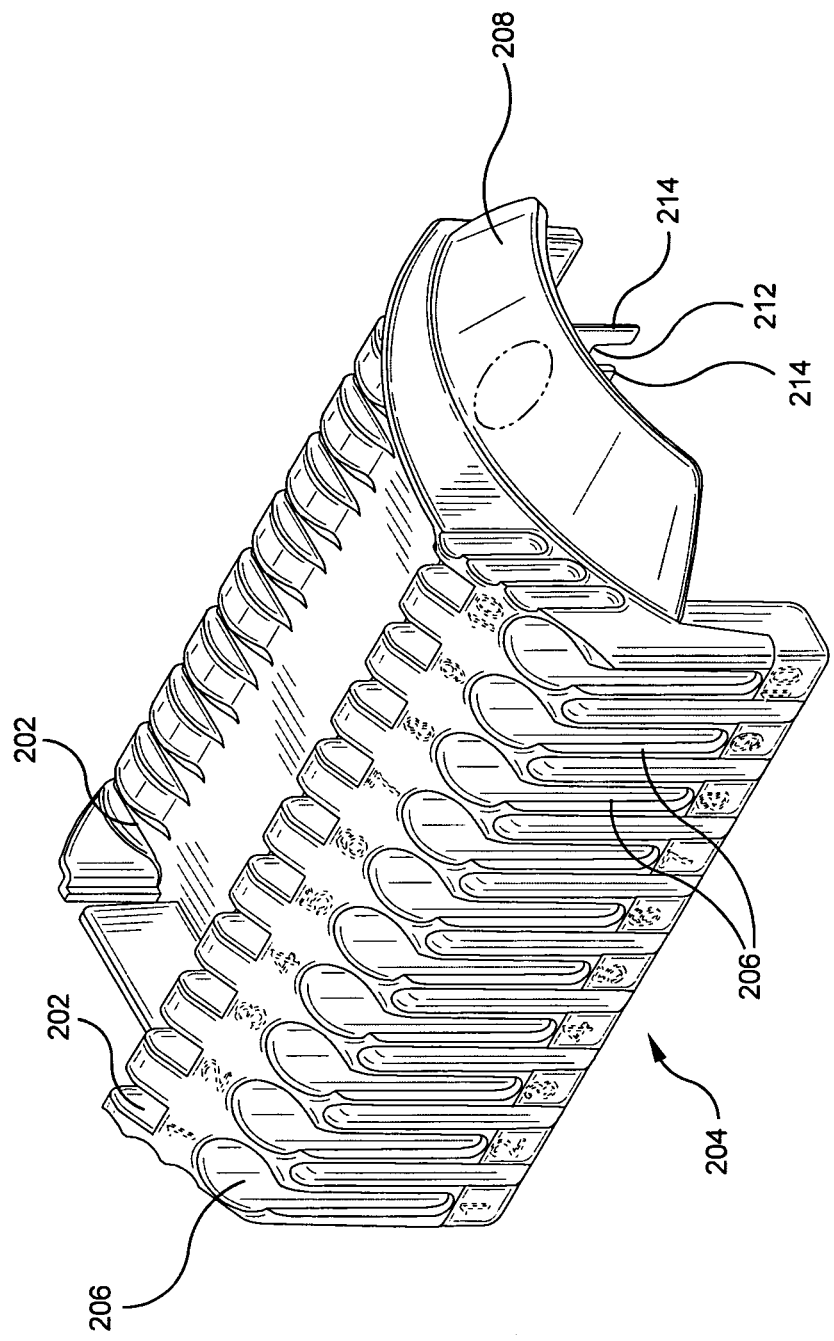
FIG. 9 is another perspective view of an empty carrier of FIG. 7.
Figure 10:
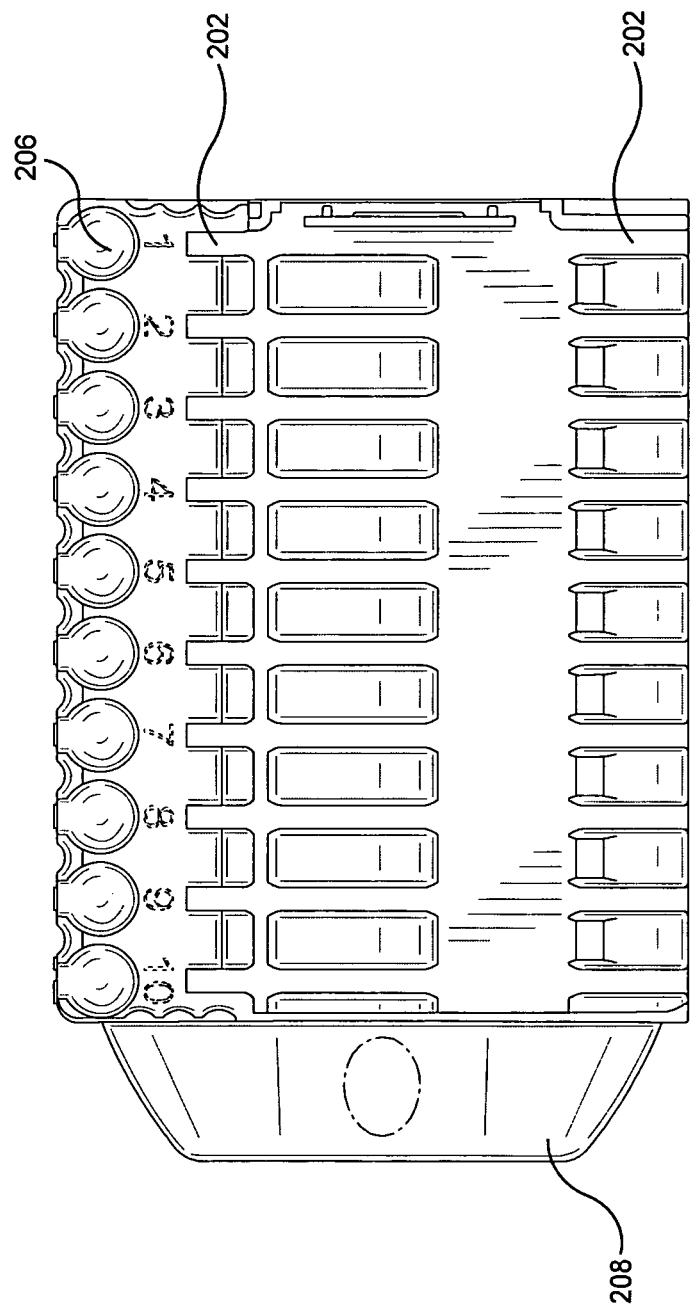
FIG. 10 is a top plan view of the carrier of FIG. 7.
Figure 11:
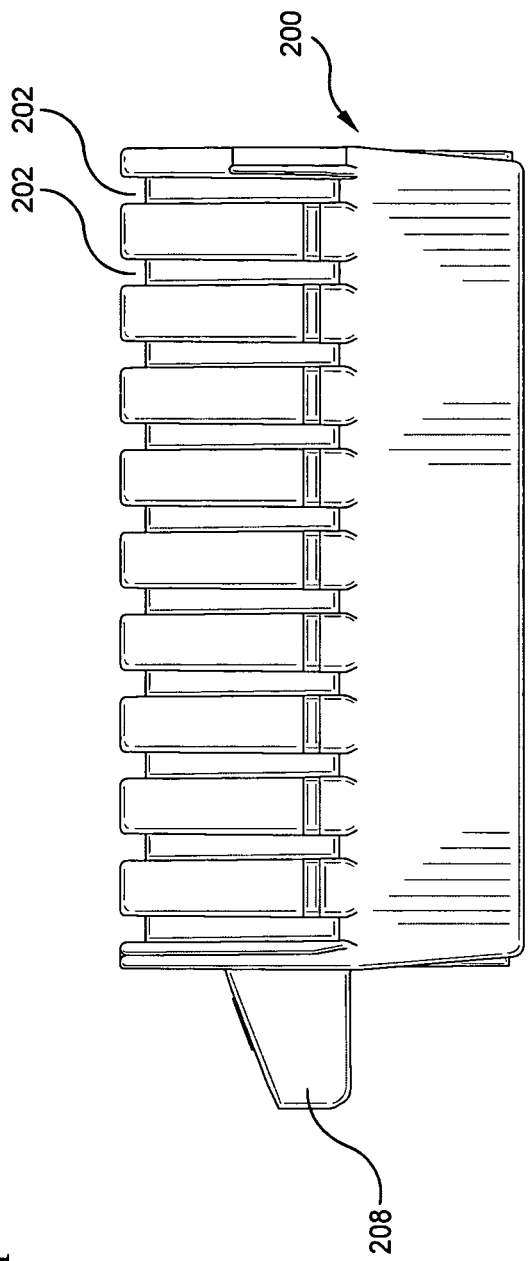
FIG. 11 is a side elevational view of the carrier of FIG. 7.
Figure 12:
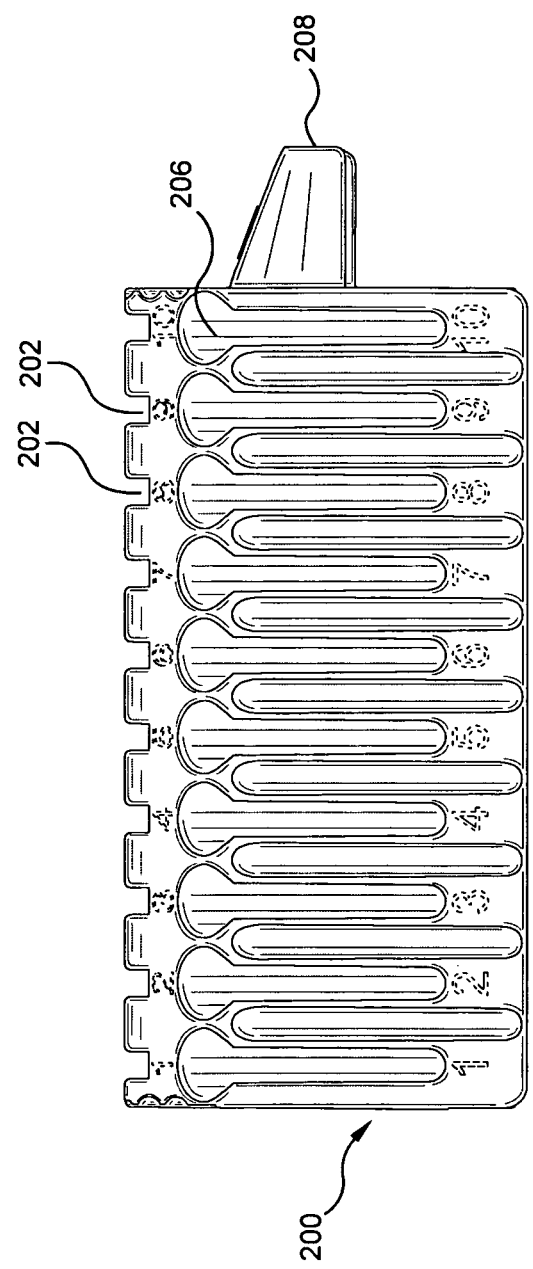
FIG. 12 is a side elevational view of the carrier of FIG. 7, opposite to that shown in FIG. 11.
Figure 15:
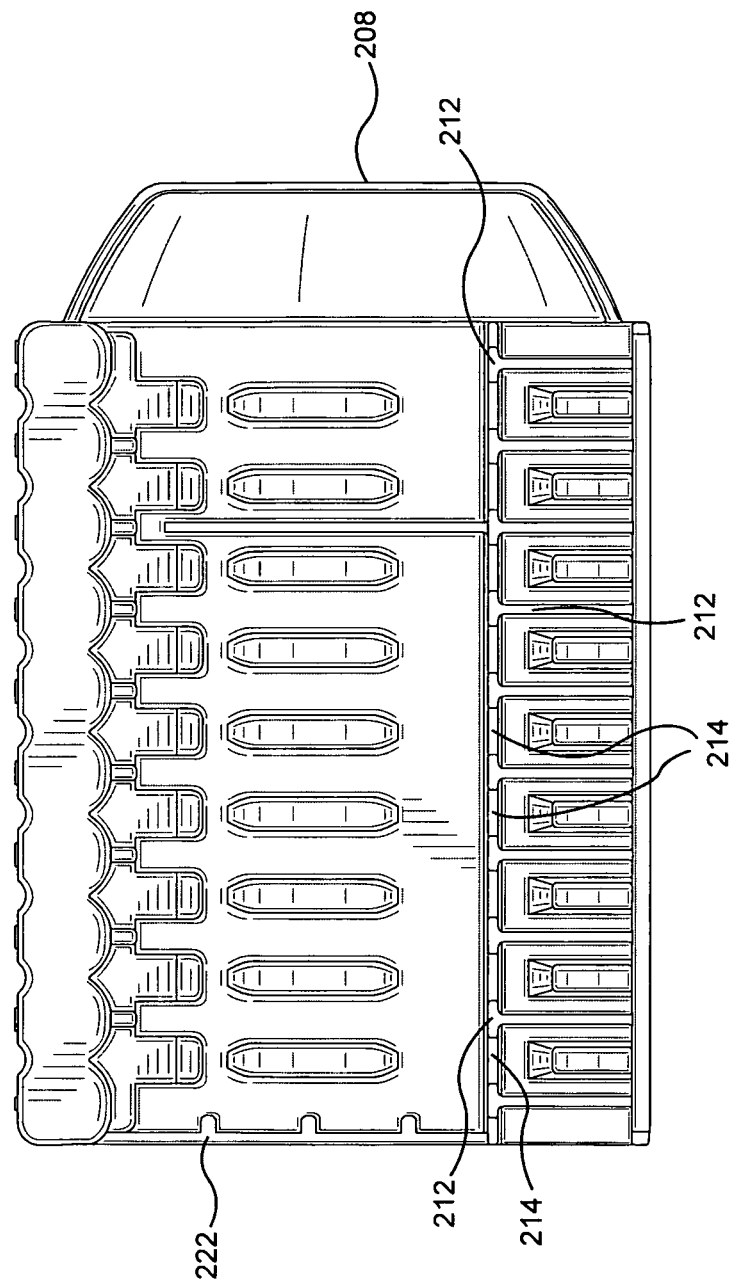
FIG. 15 is a bottom plan view of the carrier of FIG. 7, showing the rib and optical interrupt positioning features formed in registry with the test sample device receiving slots.

Referring primarily now to FIGS. 1-3B, the instrument 10 includes a set of panels 12 that cover the internal sample processing apparatus. The internal processing apparatus is described in more detail in FIG. 16 et seq. The panels 12 include a hinged vacuum door 302 that provides access to a vacuum chamber 304, which are part of the vacuum loading system 300 in the instrument. The user places a fully or partially loaded cassette 200 (a set of up to 10 test sample cards 100, each connected to an associated test tube 106 via a transfer tube 102, as shown in FIG. 7) into the vacuum chamber 304 in the manner shown in FIG. 3B and closes the vacuum door 302. A vacuum is drawn in the chamber 304 and the release of vacuum loads the fluid samples into the wells of the test sample cards 100. As shown in FIG. 4, the vacuum system 300 further includes a vacuum pump assembly 306 that supplies vacuum to the vacuum chamber 304.

The instrument further includes a hinged load/unload door 14. The user opens this door to expose a carrier loading and unloading station 16, best shown in FIG. 3A, and introduces the carrier (loaded) into the carrier and test sample device processing subsystem 50. The loaded carrier 200 (with the vacuum loading just complete) is placed inside the machine at the carrier loading station 16 for subsequent processing in the instrument (sealing, incubation, reading, disposal). The transport system 1000 in the instrument engages the loaded carrier 200 and proceeds to move the carrier as a unit to stations in the instrument as described in detail below.

The instrument further includes a waste access door 902 which is part of the card disposal system 900. The door 902 is the means by which the user gains access to a waste compartment 904. A removable receptacle in the form of a bucket (906, FIG. 16) is placed in the waste compartment 904. The test sample cards are dropped into the bucket 906 after the reading process is complete. When the bucket is full, the bucket is removed, the cards are discarded, and the bucket is replaced into the waste compartment 904.

The instrument further includes a front user access door 18, a top user access door 20, and top service panel side and rear panels, which are not relevant to the present discussion. These doors provide access for periodic cleaning of the instrument or service of components in the instrument. Access to the interior of the instrument 10 is restricted during processing for the safety of the user and to ensure uninterrupted processing of the cards. The instrument 10 monitors the status of all the doors via sensors. Doors that provide access to moving parts, such as the front user access door 18 and load/unload door 14, also have door locks that are monitored.

The vacuum door 302 and load/unload door 14 are round recessed doors. The doors pivot in opposite directions to provide an unobstructed transfer of the cassette 200 from the vacuum chamber 304 to the loading station 16. A detent in the hinge for these doors allows the door to stay open greater than 90° until the user is ready to close it. The hinges are recessed and hidden from view when the doors are closed.

Figure 1:
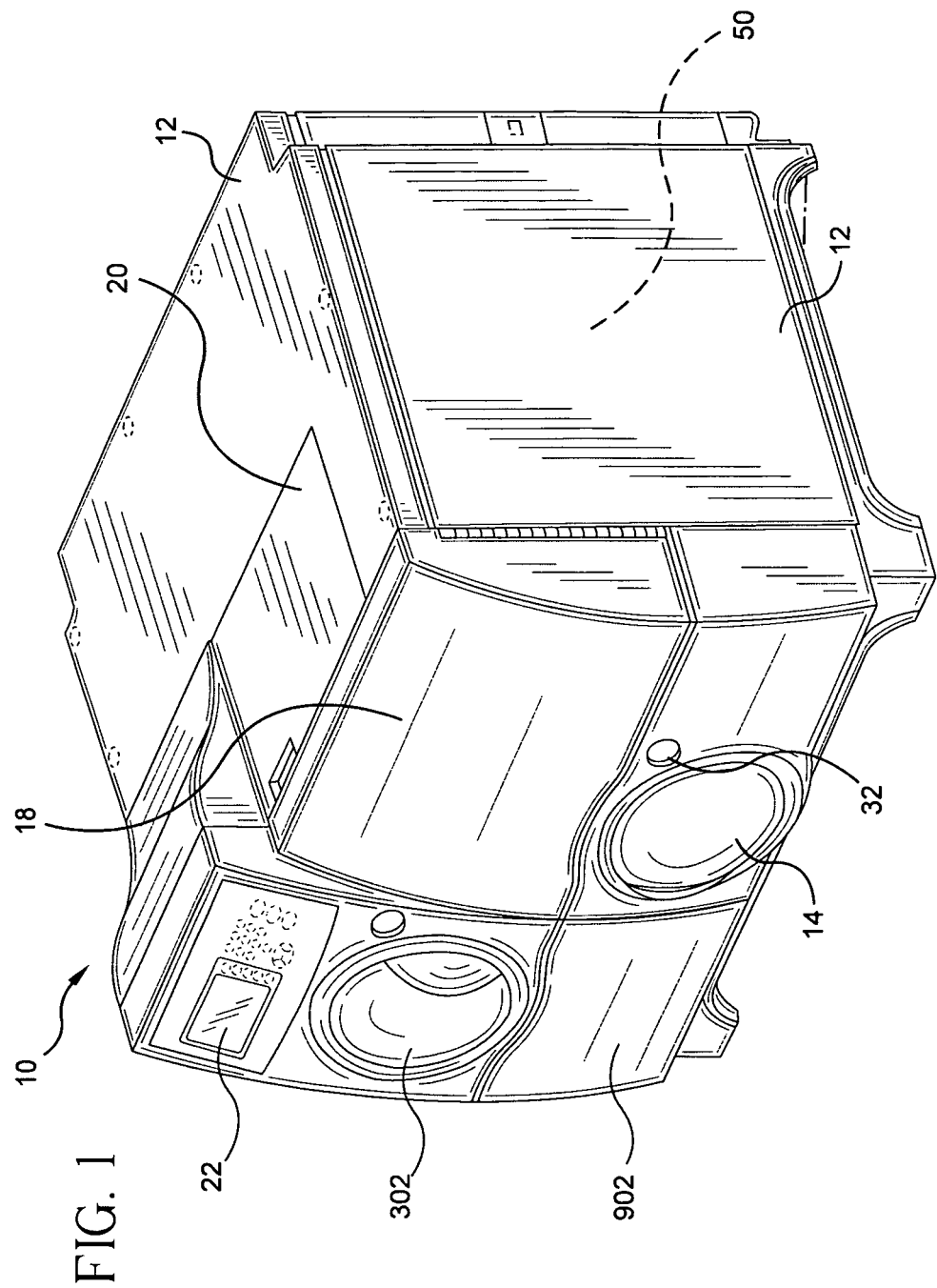
FIG. 1 is a perspective view of a preferred embodiment of a compact, integrated system for processing test samples and test sample devices. The instrument includes a vacuum station on the left for vacuum loading of test sample devices that are received in a carrier, and a separate carrier and test sample device processing subsystem on the right which processes the carrier and test sample devices after the test sample devices are loaded by the vacuum station. The sealer station is included as a module in the carrier and test device processing subsystem.
Figure 2:
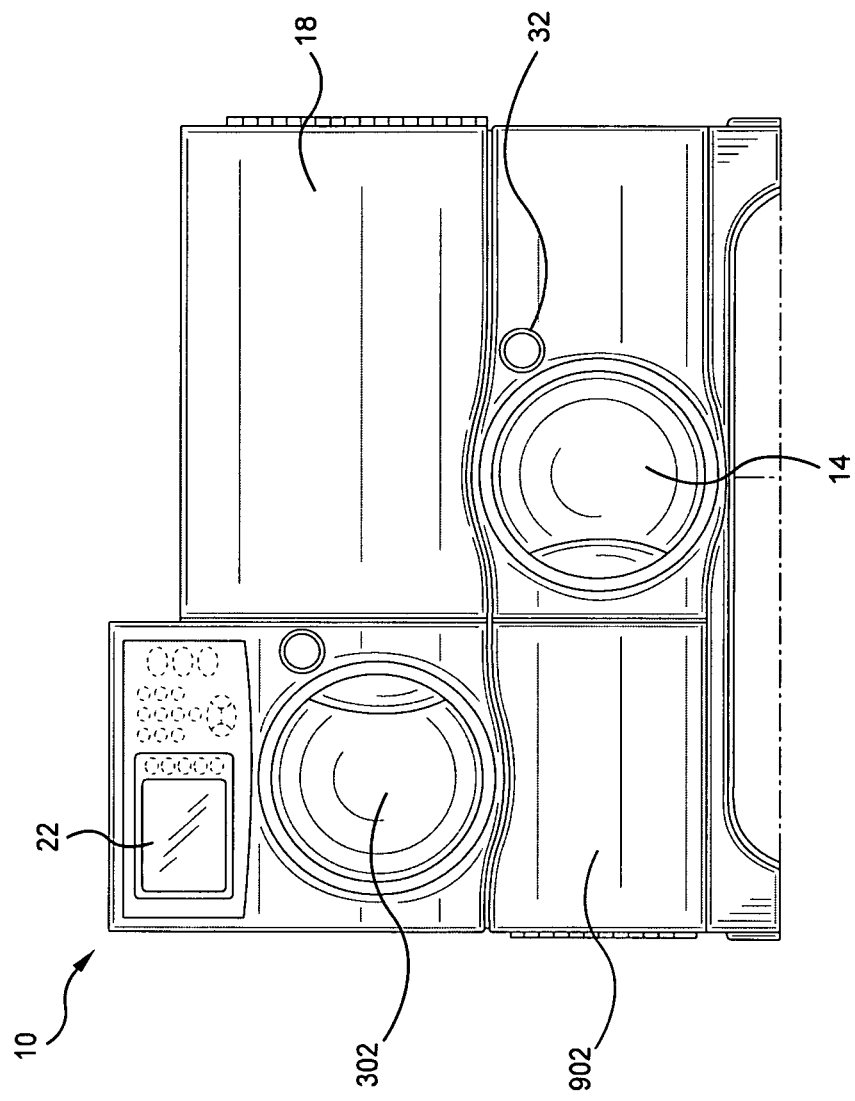
FIG. 2 is a front elevational view of the instrument of FIG. 1.

The instrument includes a compact user interface 22. The user interface includes a keypad and LCD screen, which are located on the user interface front panel, at the top left of the instrument 10 as shown in FIG. 1. The instrument uses the screen to communicate messages about its operation and its status. An audible indictor is also used in conjunction with the LCD display to notify the user when a task is complete or if an error has occurred. The keypad is used to respond to instructions, send commands to the instrument, and perform other functions. Indicator lights located next to the Vacuum Door and Load/Unload Doors provide additional status information to the user.

Test Sample Device 100 Features (FIG. 6)

The illustrated embodiment is designed to process test sample devices in the form of multi-well test sample cards. Persons skilled in the art will appreciate that the instrument, and its constituent components, can be configured to process other types of test sample apparatus, and the invention is not limited to any particular format or design for test sample apparatus.

A representative test sample card is shown in FIG. 6. The card 100 is a flat, thin object having front and rear surfaces that are covered with a clear, oxygen permeable transparent sealing tape. The card contains 64 test sample wells 104 and an internal fluid passage network 108 that connects each of the wells to a fluid intake port 110 and fluid distribution manifold. The fluid transfer tube 102 is automatically inserted in the fluid intake port 108 in the manner shown and locked in place using the teachings of O'Bear et al., U.S. Pat. No. 6,309,890. During vacuum loading of the card, the fluid sample 120 enters the card 100 from the fluid transfer tube 102 and travels along the course of the internal fluid passage network 108. The fluid sample fills the wells 104 of the cards, where the fluid rehydrates dried reagents or growth media. Under conditions of incubation, a reaction occurs between the reagents in the wells of the card and the microorganism in the fluid sample. As a result of this reaction, the transmittance of light though the wells changes. The optics in the instrument 10 periodically read the wells of the card 100 by obtaining transmittance measurements at particular wavelengths of light.

The cards for use with the illustrated embodiment are described at length in the patent literature and therefore a more detailed discussion is omitted. The reader is directed to the following U.S. Patents for further details: U.S. Pat. Nos. 5,609,828; 5,746,980; 5,670,375; 5,932,177; 5,916,812; 5,951,952; 6,309,890 and 5,804,437. Each of these patents is incorporated by reference herein.

Carrier 200 Features (FIGS. 7-15)

Referring now to FIGS. 7-15, the carrier 200 or cassette is a molded plastic component that holds a set of test sample cards 100 and associated test tubes 106. In the illustrated embodiment, the carrier 200 holds a maximum of 10 test cards in specially fitted slots 202. The front portion 204 of the cassette 200 has a test tube slot 206 for each test tube 106. The slots are numbered 1-10 across the front of the cassette for identification purposes. A handle 208 on the right side allows for one-handed carrying capability. A removable bar code label 210 is applied to the opposite side of the carrier 200 in the flat panel portion 215 (See FIGS. 7 and 14). The bar code 210 provides cassette identification when read by a bar code reader in the instrument 10. Each of the test sample cards is applied with a bar code 120, as shown in FIG. 7.

The user loads the carrier 200 with tubes 106 of patient isolates (or, more generally, a fluid sample) and test cards 100 before placing the carrier in the vacuum chamber 304 (FIG. 3A) for the filling process. The asymmetrical shape of the carrier 200 and receiving structures in the vacuum chamber 304 as shown in FIG. 3B ensures that the carrier 200 is properly loaded into the instrument (i.e., the handle 208 is towards the front of the instrument). Upon completion of the vacuum loading process, the user opens the door 302 to the vacuum chamber 304 and removes the carrier 200 from the vacuum chamber 304 and places it in the load/unload station 16.

The carrier 200 is a main component of the transport system 1000. A special block feature in the transport system 1000 enables the transport system to move the carrier through the processing stations in the carrier and test sample device processing subsystem 50 and back to the load/unloading station 16. Optical interrupt sensors in the transport system detect slots 212 (FIGS. 8, 9 and 15) that are formed into the bottom of the carrier 200. The optical interrupt sensors and the slots allow the instrument microcontroller to track the cassette location. The interrupt slots 212 are U-shaped voids formed in a rib 214 formed in the bottom of the carrier 200. Each slot 212 is positioned in registry with the position of the card directly above it. Therefore, when the interrupt sensors detect the position of a slot 212, they are also detecting the position of the associated card. This feature facilitates precise carrier positioning for automated sealing operations and automatic loading of the cards from the carrier 200 into the entrance slot in the incubation station.

Vacuum Station 300 Features (FIGS. 1-4, 7, 17)

With reference to FIGS. 1-4 and 7, the user places a carrier 200 loaded with test sample cards 100 and test tubes 106, such as shown in FIG. 7, into the vacuum chamber 304 of FIG. 3A and closes the door 302. The vacuum process is activated via the user interface 22 keypad. A silicon seal 306 on the vacuum chamber door 302 presses against the front panel surface 308, sealing the vacuum chamber 304. The vacuum pump in the vacuum pump assembly 306 (FIGS. 4, 17) starts drawing the air from the chamber 304. The air escapes from the card channels and wells via the transfer tubes and up through the suspension or fluid sample in the test tubes 106. The channels and wells inside of each card are now in a vacuum.

The vacuum station fills the card with the inoculation suspension in the test tubes 106 using vacuum displacement principles taught in Fanning et al., U.S. Pat. No. 5,965,090, the content of which is incorporated by reference herein. The rate of change of the vacuum is monitored and regulated by a pneumatic servo feedback system under microcontroller control.

In particular, after a short period, the vacuum is released at a controlled rate from the vacuum chamber. The increasing air pressure inside the chamber forces the suspension from each test tube 106 through the transfer tube 102 and into the internal fluid channels and wells 104 of the card 100. This process of course occurs simultaneously with all the cards in the carrier in the vacuum chamber. The result is vacuum loading of all cards 100 in the carrier 200. The carrier 200 is now ready for insertion into the loading station 16 of FIG. 3A and processing therein by the carrier and test device processing subsystem 50 in the remainder of the instrument 10.

Carrier and Test Sample Device Processing Subsystem (FIGS. 1, 4, 5, 16-33)

Now that the carrier 200 and test devices 100 have been processed in the vacuum station 300, the carrier 200 is now ready for placement into the loading station 16 and processed by the remainder of the instrument's subsystems, collectively referred to herein as the carrier and test sample device processing subsystem 50. This group of components includes the transport system 1000, sealing station 400, card autoloader subassembly 500, incubation station 600, card transport subsystem 700, optical reading station 800 and disposal system 900. These features will be described in further detail in this section.

Figure 16:
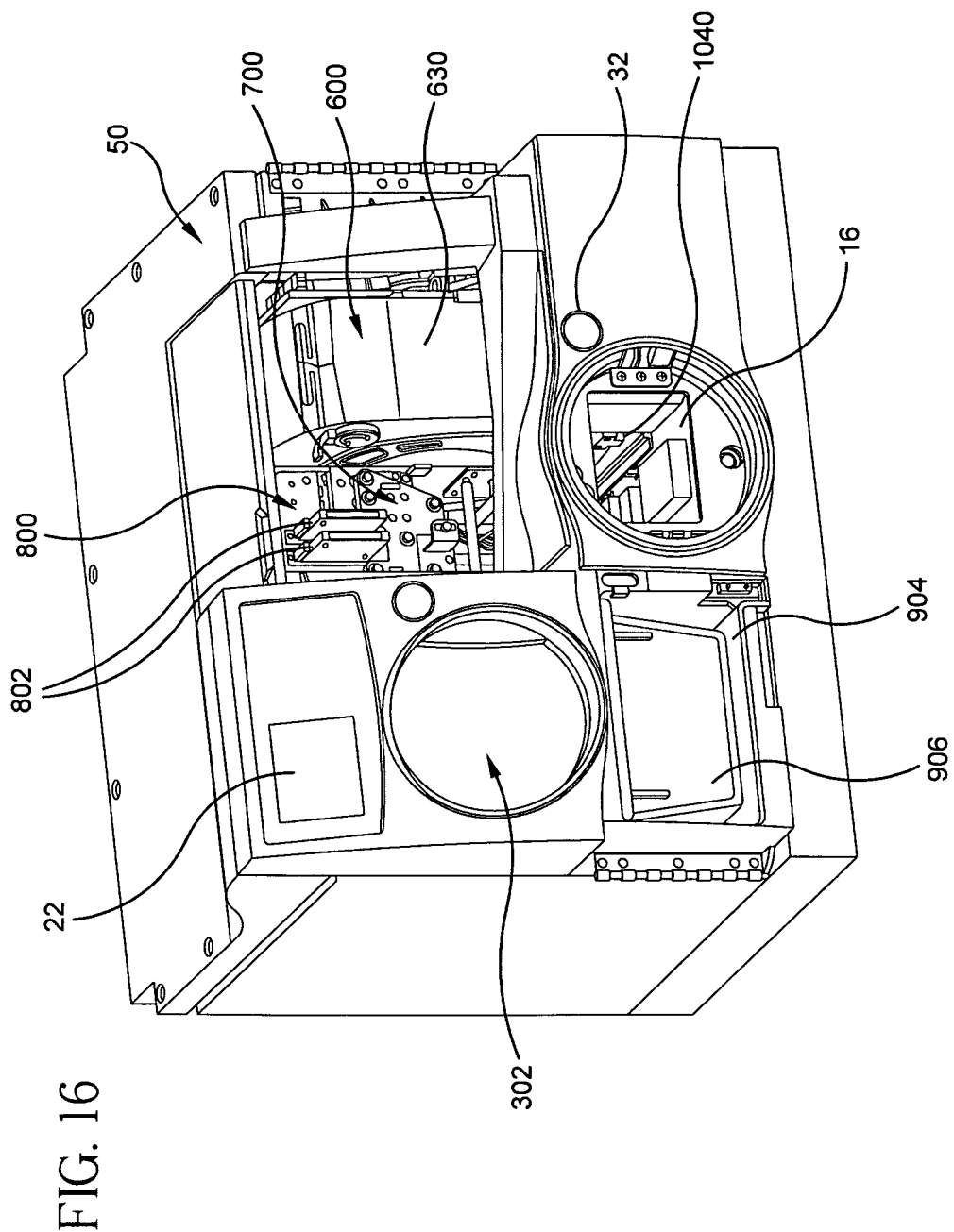
FIG. 16 is a front perspective view of the instrument of FIG. 1, with the waste collection and carrier loading/unloading doors removed, and with the front user access door removed.

Carrier Loading and Unloading Station 16 (FIGS. 1, 3A, 16)

The load/unload station 16 is where the operator manually loads the carrier of filled cards to start the sealing, incubation, and reading processes. The load/unload door 14 (FIG. 1) will remain locked at all times unless the user is ready to load or unload a carrier. The door 14 is shown removed from the instrument in FIG. 16 in order to better illustrate the loading/unloading station 16.

The loaded carrier 200 (FIGS. 3B, 7) is loaded into the instrument 10 through the open load/unload station door 14. A reflective sensor 1040 (FIG. 17) in the load area is used to sense the presence of a carrier 200 in the load/unload station 16. An indicator light 32 above the load/unload station 16 indicates the status of the load/unload station to the user. Once the door 14 is closed, the processing cycle automatically initiates.

The transport system 1000 (FIGS. 29-33) moves the carrier 200 by pulling or pushing it through each processing station within the instrument in the manner described below. The instrument microcontroller keeps track of where the carrier 200 is located and the status of the transport system utilizing the slots 212 molded into the bottom of the carrier (described above) and optical sensors 1050 A-C (FIG. 29) that are strategically placed in the transport system 1000. The transport system 1000 moves the carrier from the load/unload station 16 to a bar code scanner where the carrier bar code (FIG. 7) and test sample bar codes are read, the sealer station 400, the card autoloader station 500 where the cards are loaded into the carousel incubation station 600, and back to the load/unload station 16 for removal of the carrier 200 and the test tubes plus transfer tube 102 remnants. The carrier is parked at the load/unload station 16, the door 14 unlocked and the operator notified by the load/unload indicator light 32. The carrier 200 can then be removed allowing disposal of the processed test tubes 106 and transfer tube 102 waste, making the carrier ready for testing of the next batch of test cards and associated fluid samples.

Bar Code Reader Station 60 (FIGS. 4, 5, 20, 17)

Figure 17:
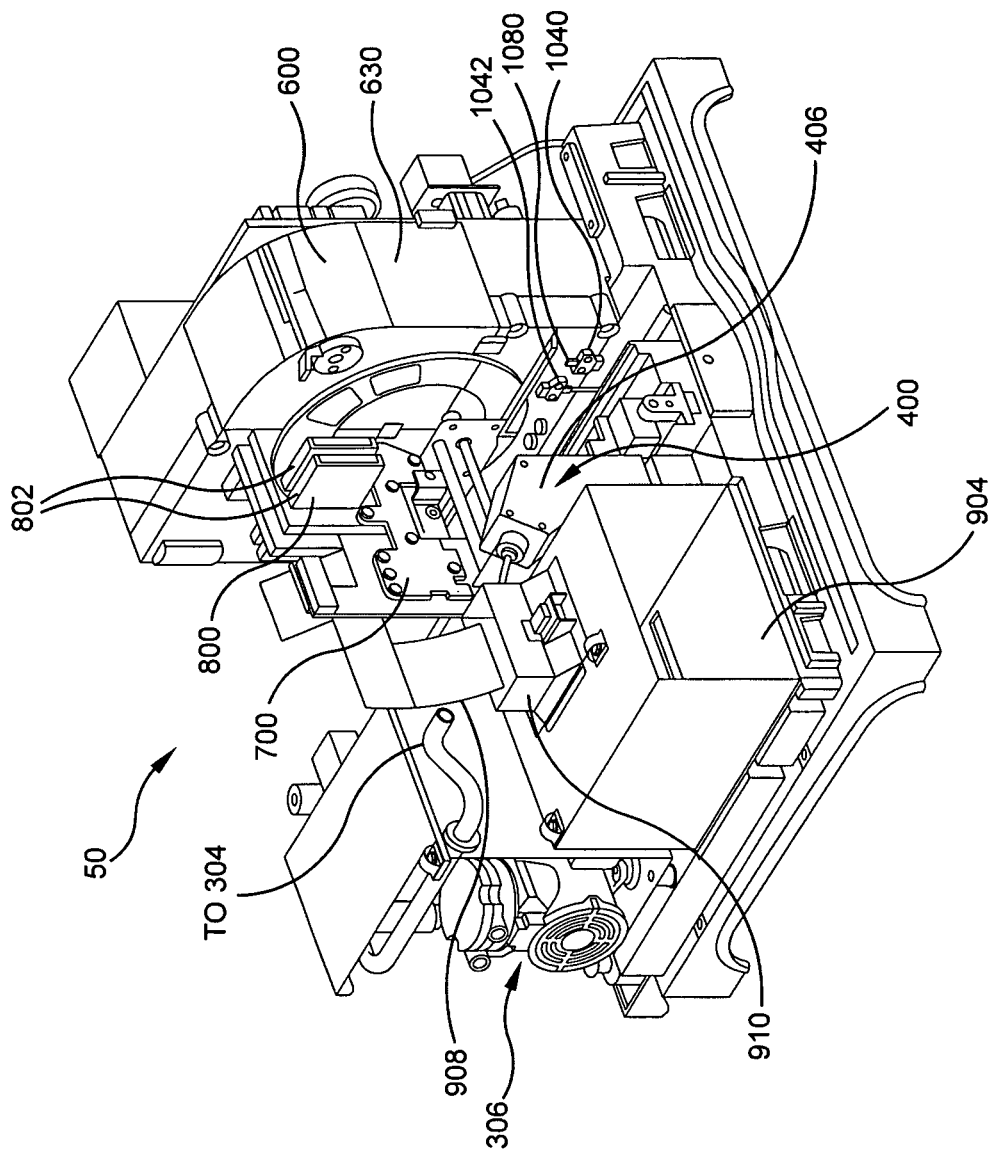
FIG. 17 is a perspective view of the instrument of FIGS. 1 and 16 with all of the instrument panels and doors removed, showing generally the front and left hand sides of the instrument, to better illustrate the subsystems and subcomponents of the instrument, in particular the vacuum, waste disposal, and test sample device reader subsystems.
Figure 18:
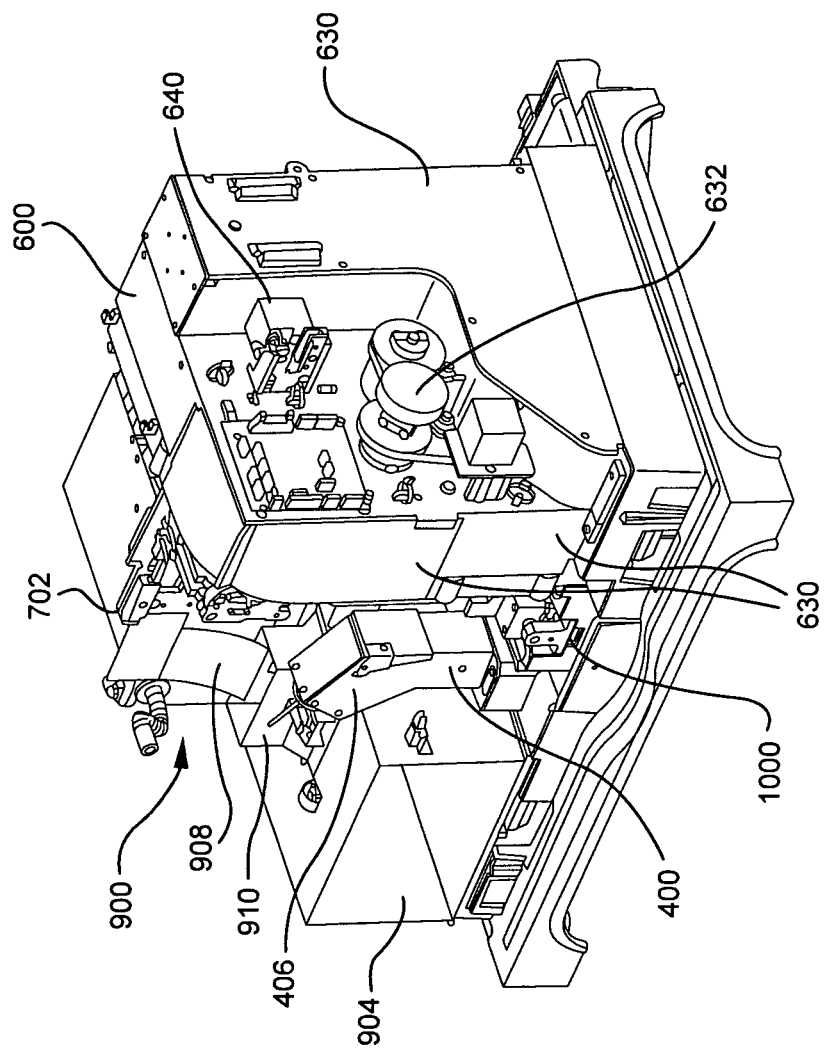
FIG. 18 is another perspective view of the instrument of FIGS. 1 and 16 with all of the instrument panels and doors removed, showing generally the front and right hand side of the instrument, in order to better illustrate the subsystems and subcomponents of the instrument, in particular the waste disposal, sealer, and incubation station subsystems.
Figure 19:
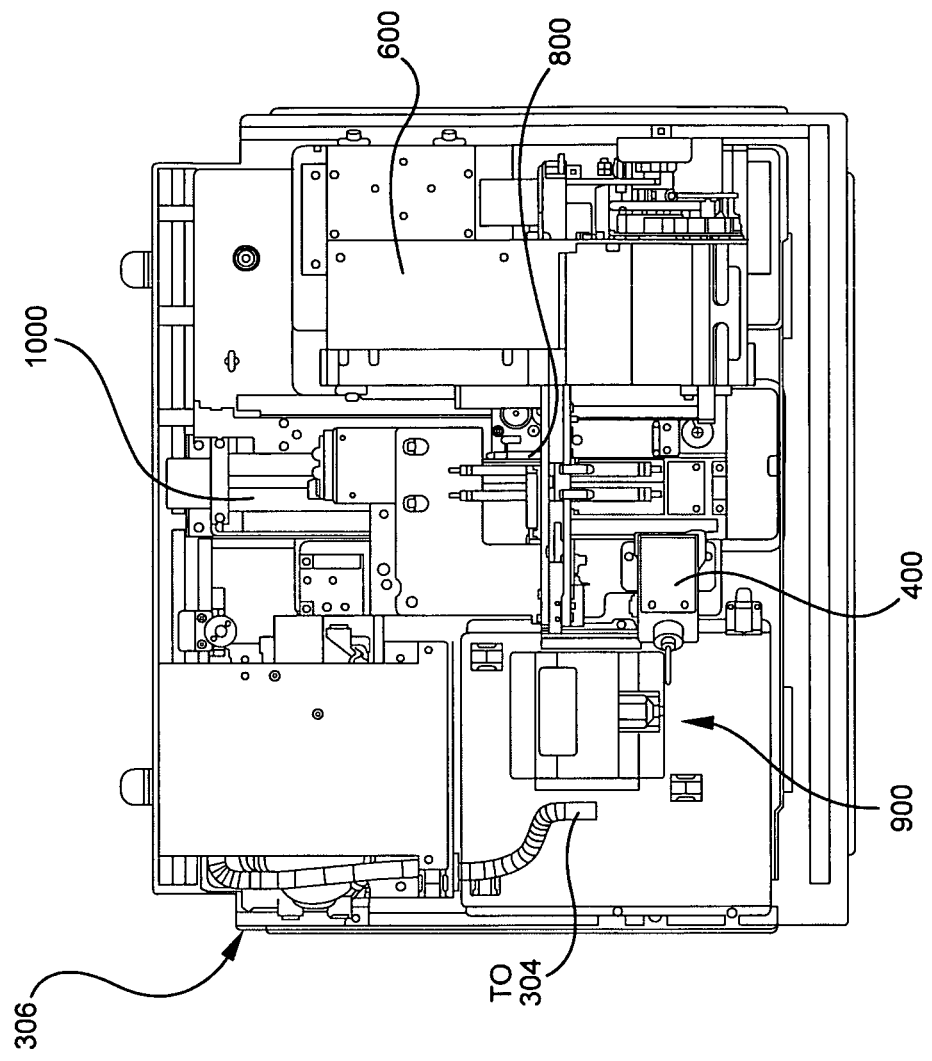
FIG. 19 is a top plan view of the instrument of FIGS. 16 and 17.

A bar code reader station 60 (FIGS. 4, 5) is positioned in the instrument 10 generally below the reading station 800. The station 60 automatically scans the bar code information on each carrier 200 and test card within the carrier 200 (see FIG. 7) as they pass through the station. The bar code reader station 60 consists of a bar code scanner 62 (FIG. 20) and a card sensor 1042 (FIG. 17). The card sensor 1042 is located on the housing of the incubation assembly 600 as close to the cards in the cassette as possible. The card sensor 1042 confirms the presence of a card 100 in the carrier 200 and the slot location. The slots 212 in the bottom of the carrier allow the transport system 1000 to position each card in front of the bar code scanner 62.

As shown in FIG. 7, each card 100 has a factory applied bar code 120 that includes information such as test type, lot number, expiration date and a unique sequence number. When the card bar codes 120 are scanned at the separate workstation at the time of loading cards into the carrier 200, the instrument's bar code reader 62 provides an additional level of security by verifying that the cards 100 are loaded as indicated by the user. If the bar codes are not scanned at the separate workstation ("load and go" mode), the lab technician's worksheet can be used for verifying that cards 100 are loaded in the carrier 200 as indicated.

Successfully scanned carriers 200 and test cards 100 are allowed to continue to the sealer station 400. Carriers 200 and cards 100 that cannot be read at the station 60 due to errors such as missing or damaged bar codes, expired cards, and unsupported card types, are returned to the load/unload station 16 and the user notified via the user interface 22 or indicator light 32. The user is given the opportunity to correct the problem and reload the carrier 200 within a limited amount of time.

Sealer Station 400 (FIGS. 4, 6, 7, and 17-24, 35)

With reference to FIGS. 4, 6, 7, and 17-24 and 35, before a test card 100 can be incubated and read, the wells 104 of the test sample card must be sealed off from the outside environment. The sealer station 400 provides this function for all cards loaded into the carrier 200, one at a time. The sealer station 400 melts and seals the transfer tube 102 using a retractable heated nichrome wire 402, and thereby seals the cards. This operation will now be described in further detail.

After a carrier 200 is loaded into the instrument, a transport block in the transport system 1000 engages with the carrier 200 and pulls the cassette 200 along the transport system track through a carrier sensor 1040, a card sensor 1042, and the bar code scanner 62. If the carrier passes inspection, it is moved back along the transport system 1000 track toward the load/unload door 14 where the sealer station 400 operates to cut and seal all the cards in the carrier 200.

In particular, as the carrier 200 moves through the station 400, the hot wire 402 is translated downwardly and at an angle through an aperture 404 in an enclosure or housing 406 to the same elevation of the transfer tubes 102 in the carrier 200, and thereby exposed to each transfer tube 102. As the carrier 200 is slowly advanced by the carrier transport system 1000 each transfer tube is forced past the hot wire 402. The hot wire 402 causes the plastic transfer tube 102 to melt, separating the majority of the transfer tube, which falls into the test tube 106. The remainder of the transfer tube forms a short, sealed stub (e.g., 1.5 mm in length) extending outward from the fluid intake port 110 in the card (FIG. 6). At the completion of the sealing processing, power is cut off to the wire 402 and it is retracted back into it's housing 406 to eliminate user contact. The temperature of the wire 402 is controlled by a microcontroller controlled constant current source, as described in Karl et al., U.S. Pat. No. 5,891,396, which is incorporated by reference herein.

The overall operation of the sealer to cut the transfer tubes 102 is similar to the process described in the Karl et al. '396 patent. As cards 100 move past the sealer, the transfer tubes 102 are forced past the hot wire 402 melting the plastic and sealing the cards. The wire 402 and its associated assembly 408 then retracts into the housing 406. The carrier 200 is then moved to the card autoloader station 500, which moves the cards laterally off of the carrier 200 and into the entrance aperture of the incubation system 600.

The sealer assembly 400 is unique in several respects: a) its method of electronic control, b) its mechanical alignment, c) a preloading feature where each card is biased against fixed structures in the instrument prior to cutting and sealing the transfer tubes, and d) features preventing unauthorized user access.

As for feature a), a microcontroller ensures reliable cutting and sealing by maintaining a constant current in the hot wire 402 while retracting or extending the wire 400 through the aperture 404 per the card/cassette cycle requirements.

As for feature b), the sealer housing or enclosure 406 orients a wire assembly 408 and associated drive mechanism 410 at an angle allowing alignment of the wire 402 using only one motor 412 to control the horizontal and vertical position. The wire alignment is achieved by adjusting the mounting of the housing 406 in the instrument or the alignment of the drive mechanism 410 to the housing, and/or setting the limit positions of the motor 412 in firmware.

Figure 36:
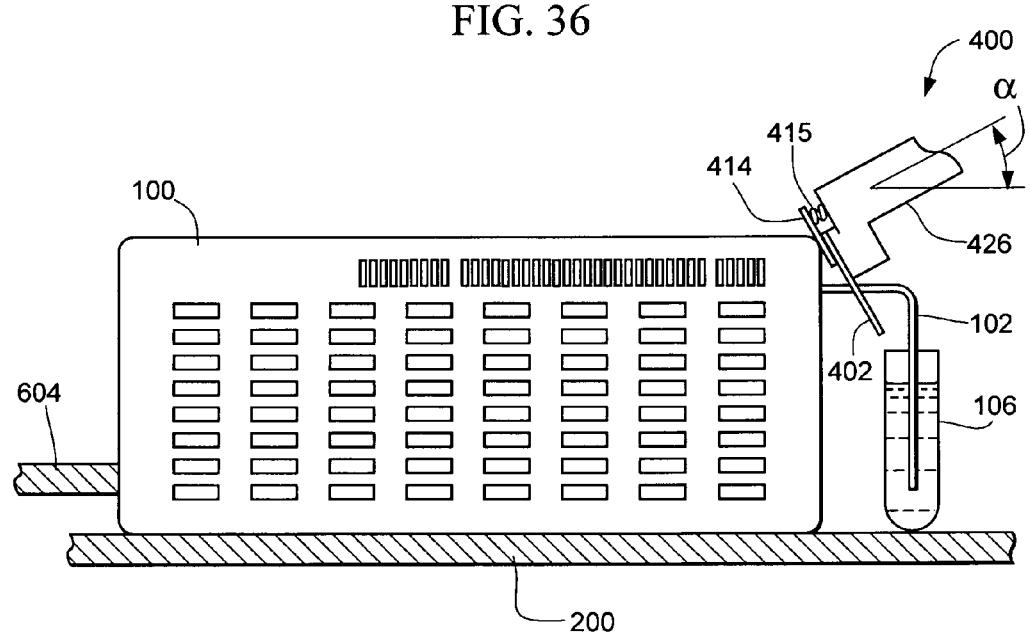
FIG. 36 show the action of the spring loaded pad of the sealer of FIG. 35 biasing the card against the fixed structure in the instrument to produce a uniform stub length of the sealed transfer tube.

As for feature c) and d), the wire 402 and its associated assembly 408, and the drive mechanism 410 are ordinarily placed within the housing 406. A shield 416 covers the entrance aperture 406. When a card is in position for sealing, the motor 412 is energized and the motor operates to move the wire assembly 408 down and at an angle through the aperture 406. This action causes the shield 416 to move out of the way to a retracted position. A spring-loaded pad 414 in the wire assembly 408 and located in front of the wire 402 makes contact with the edge of a card 100 and preloads or biases the cards 100 using a coil spring 415 against a fixed structure or stop in the instrument. The fixed structure is in the form of a rail 604 extending lengthwise along the face of the incubation station 600 housing 602. (See FIG. 36). Other constructions are of course possible. The wire 402 then cuts through the transfer tube to produce uniform stubs lengths as the cards 100 are moved past the stationary sealer wire 402. After the sealing operation is completed, the motor 412 is energized to retract the wire assembly 408 into the housing 406. As it does so, the rotating shield 416 retracts by gravity to a closed position covering the aperture 404. This covering of the aperture 404 prevents the user from gaining access to the retracted hot wire 402.

As the carrier 200 approaches the sealer station, the transport system 1000 slows its movement to a slow speed. The motor 412 in the sealer station 400 energizes to move the wire subassembly 408 through the aperture 404 and expose the wire 402. The pad or "shoe" 414 is mounted approximately 2.0 mm in front of the sealer wire 402. The shoe is spring loaded by a compression spring 415 shown in FIG. 22. The shoe or pad 414 mounts with a single shoulder screw 420 and incorporates an anti-rotation feature. As the card 100 approaches the hot wire 402, the shoe 414 makes initial contact with the card, deflecting the spring 415 and preloading the card 100 against the rail 604 (FIG. 27) on the incubation assembly panel 602. This insures consistency in transfer tube stub length. Forward motion of the carrier 200 past the hot wire 402 cuts the transfer tube 102, melting the plastic transfer tube 102 and sealing each card. After all the cards 100 in the carrier are sealed, the transport system 100 again reverses direction along its track and each of the cards is placed in registry with the card autoloader system 500 for loading into carousel incubation station 600 to incubate.

The sealer wire 402 in the preferred embodiment is a heated 18 Gauge Chromel A wire mounted on a sliding block mechanism 422 inside the metal enclosure or housing 406. The housing 406 positions the drive mechanism 410 at an angle, and locates the extended sealer wire/preload shoe 414 at the correct height, and prevents user access to the sealer wire 402 and drive mechanism. The drive mechanism 410 is mounted at an angle (α in FIG. 36) to simplify the horizontal and vertical alignment. A stepper motor 412 extends the hot wire mounting-block 426 at a 30° angle from horizontal to simultaneously adjust the horizontal and vertical position. This angle can of course vary in different embodiments and could vary for example between 20 and 70 degrees. The exact alignment of the sealer wire 402 is adjustable by firmware controlling the limits of the motor 412 to ensure a uniform stub length between 1.0 and 2.5 mm. When the cutting and sealing operation is finished, the stepper motor 412 retracts the hot wire assembly 408 until a flag 424 on the block 426 in the drive system is sensed by home position sensor 428 (see FIG. 22). The assembly includes a chain 448 that serves to protect a wire 446 supplying current to the cutting wire 402.

As the hot wire assembly 408 and mounting-block 426 is retracted, the rotating shield 416 drops down by gravity and covers the housing opening 404. The shield 416 has a tang 430 and flange 452. The flange 452 is positioned inside the elongate opening 454 in the housing 406 when the unit is assembled. The flange 452 contacts the shoulder 426 of the mounting-block 426 as the block 426 nears the retracted home position. The tang 430 and flange 452 prevents the user from lifting the shield 416 and gaining access to the hot wire. When the sealer motor 412 is energized, it causes the pin 462 to slide through the slot 460 in the drive mechanism 410 and thereby extends the hot wire mounting-block 422. The protective shield 406 is pushed open by the contact between the face of the block 422, which causes the shield to rotate upward, exposing the hot wire 402 and preload shoe 414. The microcontroller supplies a constant current to the wire 402 sufficient to produce the proper temperature for cutting through the transfer tubes as the cards pass by, melting the plastic and leaving a small stub of the tube to seal the interior of the card from the atmosphere.

Card Autoloader Station 500 (FIGS. 20 and 25-28)

Referring now to FIGS. 20 and 25-28, the instrument 10 further includes a card autoloader station 500 that loads sealed cards 100 into the incubation station 600. After the cards have been sealed, the carrier 200 is moved to the autoloader station 500. The slots 212 in the bottom of the carrier 200 (FIG. 8) allow the transport system 1000 to position each card directly in front of the incubator 600 entrance slot 610, shown best in FIG. 28. The slot in the carrier is determined and tracked automatically by the instrument's internal microcontroller.

The autoloader station 500 includes a reciprocating, motor-driven pusher mechanism 502, located above the carrier 200. The mechanism 502 pushes the card 100 laterally off of the carrier 200 into the carousel (not shown) in the incubation station 600. The incubation station 600 carousel is a circular carousel oriented on its side (rotating about a horizontal axis) having 30 or 60 slots. One of the slots is positioned at the 6 o'clock position directly in alignment with the card entrance slot 610. The pusher mechanism 502 returns home and the transport system 1000 and carousel index to the next card position. The loading of the next card in the carrier 200 proceeds in the same fashion. Upon completion of loading all the cards, the transport system 1000 returns the carrier 200 and test tubes 106 to the load/unload station 14 and notifies the user via the indicator 32 and user interface 22.

Figure 27:
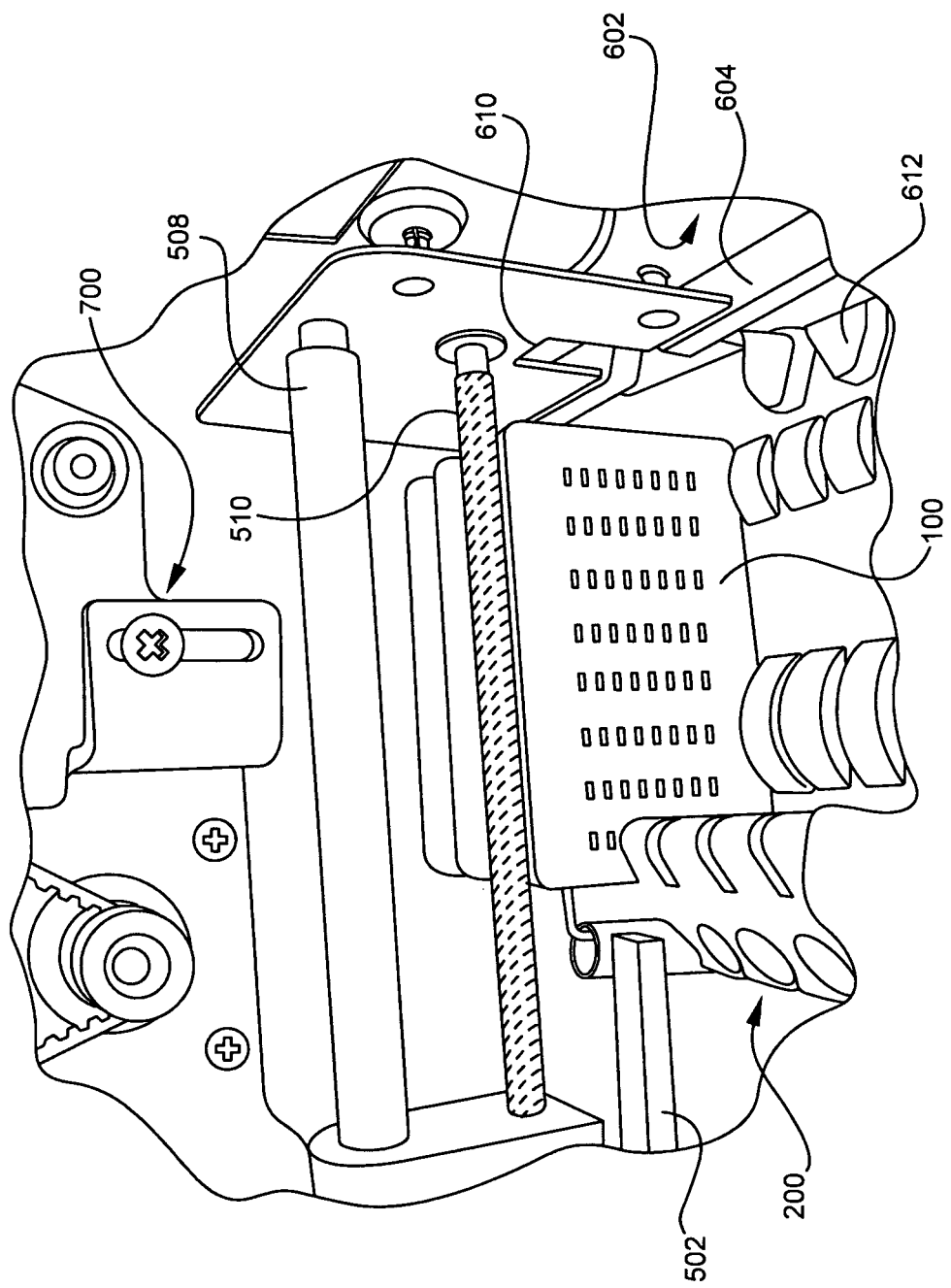
FIGS. 27 and 28 are two perspective views showing the operation of the card autoloader subassembly of FIGS. 25 and 26 loading cards into the incubation station of the instrument of FIG. 1.
Figure 28:
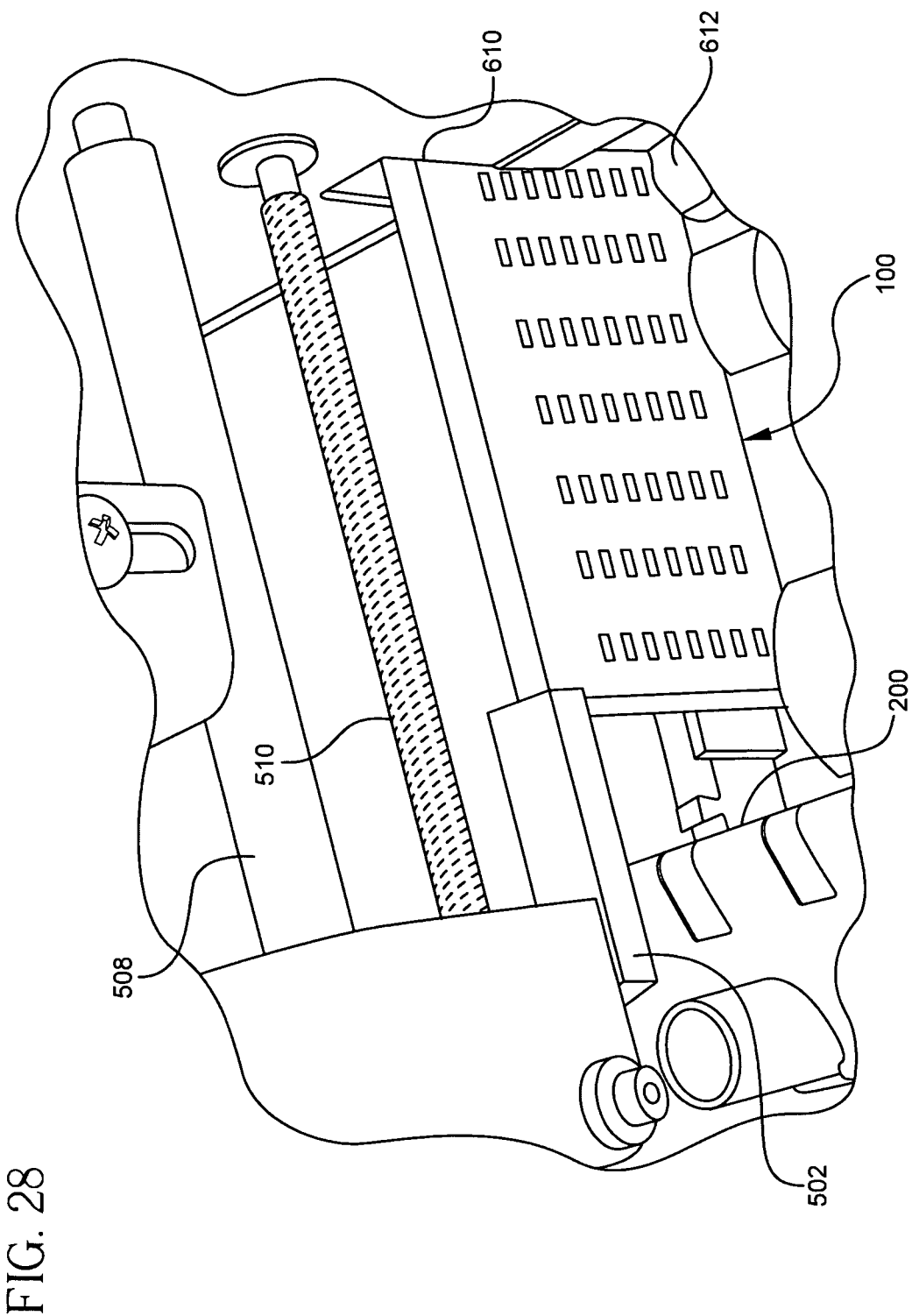

Referring now in particular to FIGS. 25-28, the autoloader includes a motor 504 that drives a block 506 attached to the card pusher mechanism 502. The block 506 has internal threads that engage a threaded shaft 510 extending laterally across the path of the carrier 200. As the motor 504 drives the block 506, the block 506 and attached pusher 502 slides along a guide 508. The pusher 502 contacts the cards 100 in the carrier and inserts them automatically into the slot 610 in the incubation station 600. The tips 512 and 514 of the shaft 510 and guide 508 are received in apertures in a plate 612 mounted to the housing 602 of the incubation station as shown in FIGS. 27 and 28. A pair of guides 612 guide the cards 100 into the slot 610.

Incubation Station 600 (FIGS. 16-20)

The incubation station 600 in the instrument 10 will now be described in conjunction with FIGS. 16-20. The incubation station includes a circular carousel. The circular carousel is not shown in the drawings, as it is covered by a removable access cover 630 forming an incubation enclosure. The carousel is rotated by means of a motor 632, shown in FIG. 18. The structure and operation of the incubation station 600 and its associated carousel is basically the same as set forth in the patent literature, see U.S. Pat. Nos. 6,024,921; 6,136,270 and 6,155,565, the contents of which are incorporated by reference herein. See also U.S. Pat. No. 5,762,873. Accordingly, a detailed description of the construction of the incubation station 600 is omitted for the sake of brevity.

Once the test sample cards have been sealed and the cards loaded into the carousel via the entrance slot 610, they remain in the carousel for the duration of the test period (up to 18 hours) or until the predetermined time allotment is met. The time allotment varies for each reagent or type of card. The carousel is contained in a temperature-controlled chamber (incubator), enclosed by the access panel 630.

The carousel itself in a preferred embodiment is composed of four quadrants (called quadrocells or quads), as taught in U.S. Pat. No. 6,136,270, together capable of holding up to 60 test cards within the incubator. Alternative configurations are possible. Positioning of the carousel is accomplished by optical sensors located at the top and bottom of the carousel, which read positioning slots on the outside edge of the carousel. Each carousel quadrant can be removed independently for cleaning. However, all four carousel quads must be in place in order for cards to be processed.

The incubator system regulates the temperature of the cards in the carousel. The temperature is monitored and controlled through the use of precision thermistors monitored by a microcontroller maintaining at an average carousel temperature of 35.5±1° C. Access for a separate user installed probe thermometer has been provided to the front of the Incubator Cover. This allows the user to verify the accuracy of the incubator temperature using an independent calibrated thermometer. The rotating carousel system delivers test cards to the card transport system 700, which moves the cards to the reader station 800 four times an hour until the test is completed. The reader head optics scans each card and returns them to the incubator. The carousel includes a card eject mechanism 640 shown best in FIG. 18 that ejects a card from the 12 o'clock position in the carousel and places it in a test card transport system 700 (FIG. 16) for transfer to the optics station 800 and return to the incubation station 600. This is the same as described in e.g., U.S. Pat. No. 5,762,873.

Figure 20:
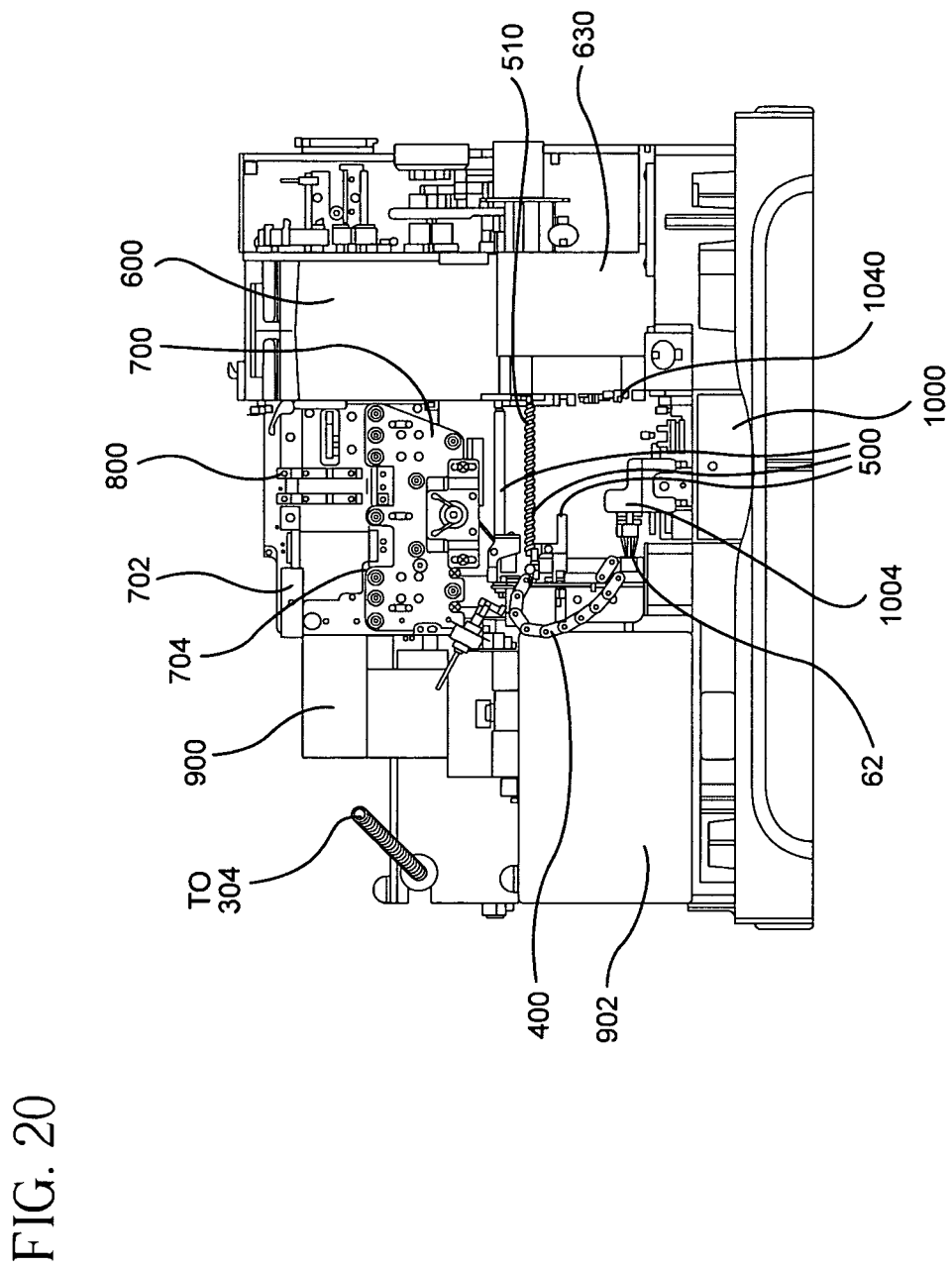
FIG. 20 is a front elevational view of the instrument of FIGS. 16-19.
Figure 21:
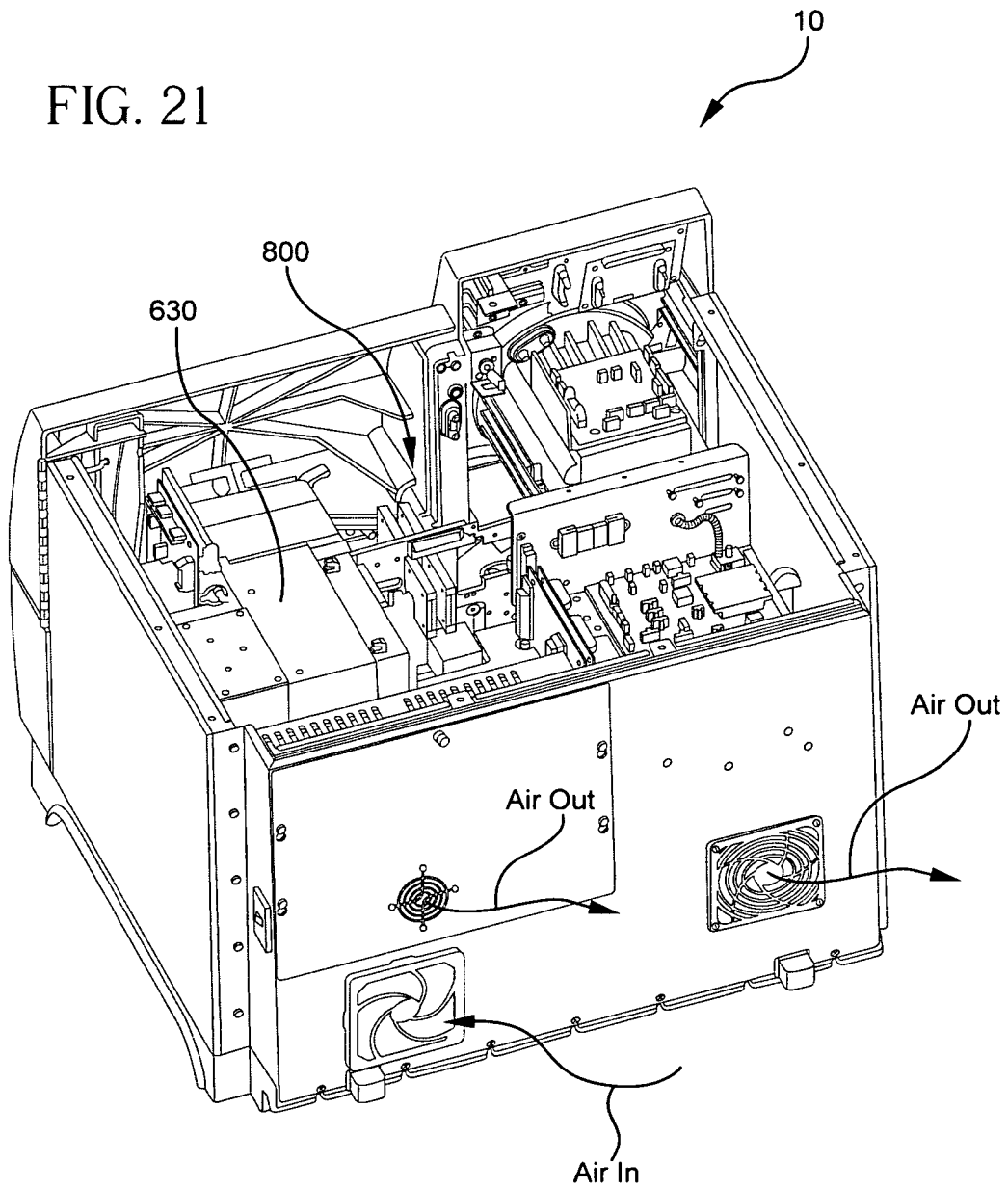
FIG. 21 is a perspective view of the top of the instrument with the top panel removed, in order to better illustrate the various components and subsystems of the instrument.
Figure 22:
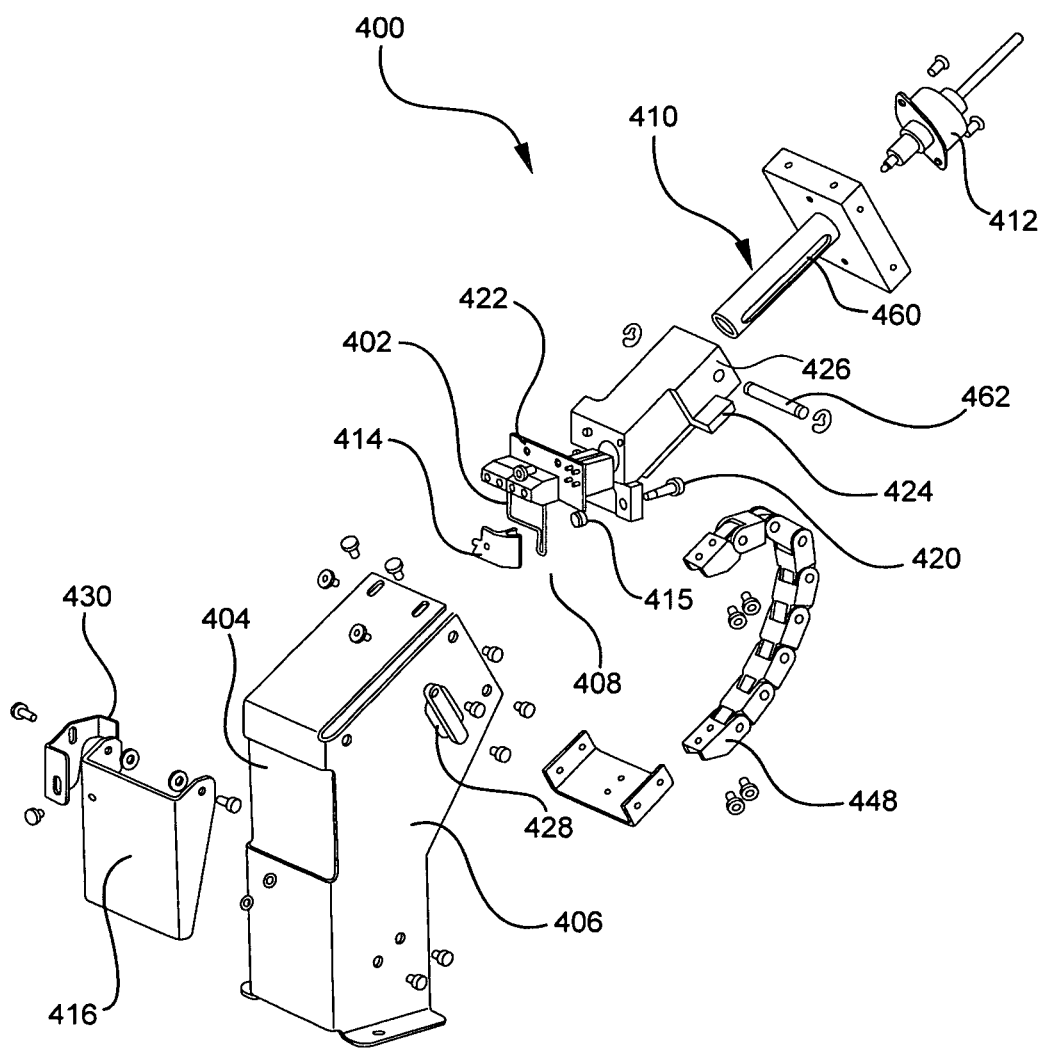
FIG. 22 is a perspective, exploded view of the sealer station of FIG. 20.
Figure 23:
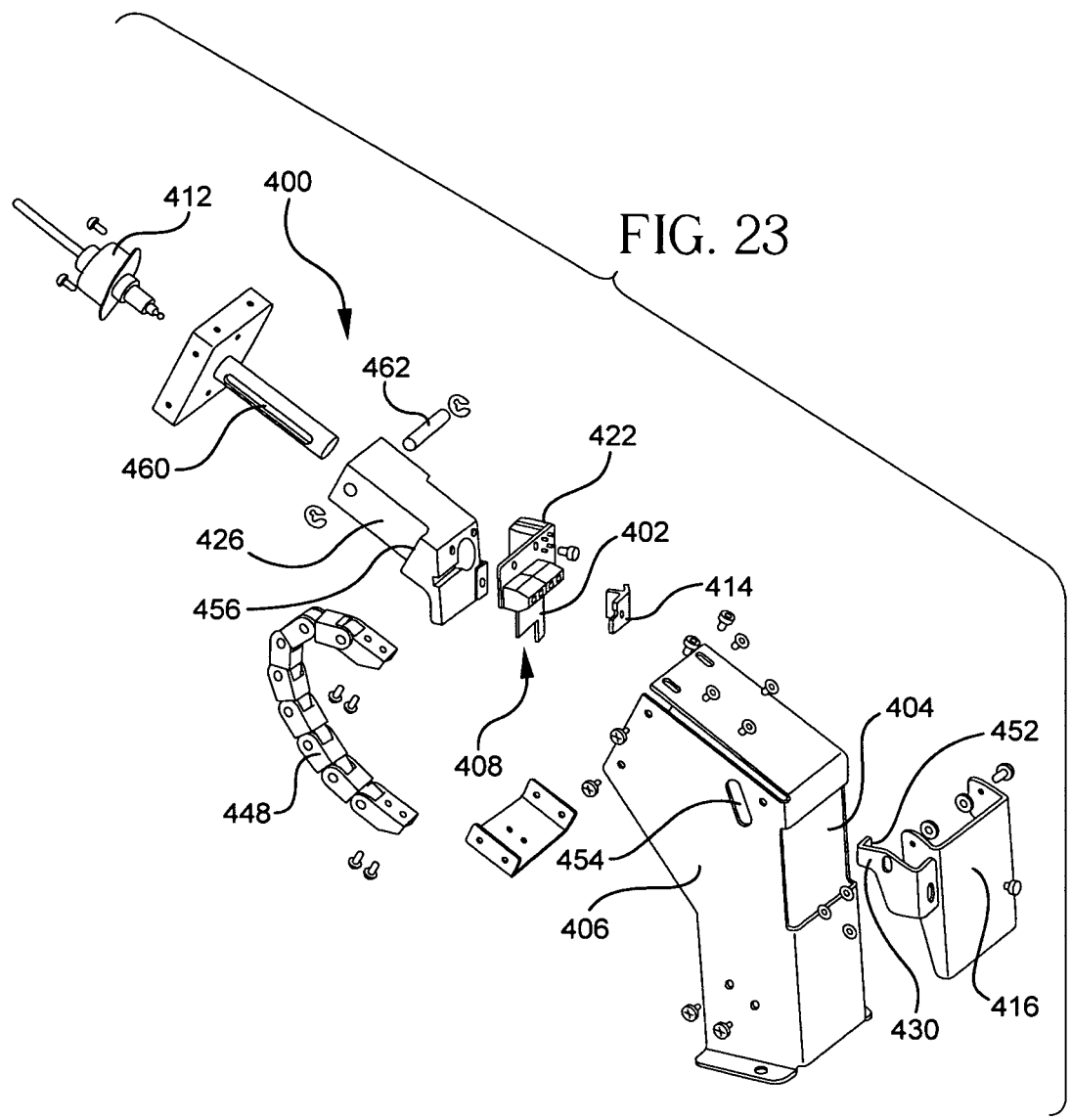
FIG. 23 is another perspective, exploded view of the sealer station of FIG. 22.
Figure 24:
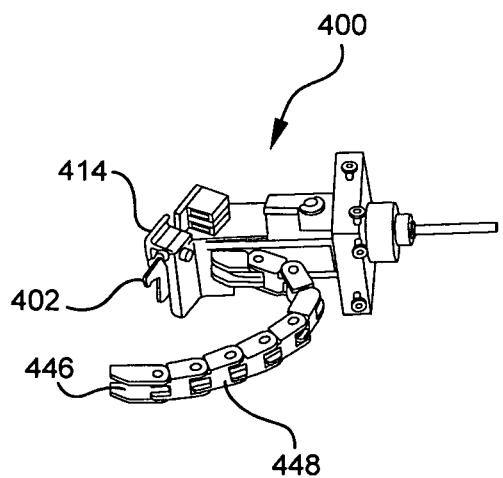
FIG. 24 is an assembled, perspective view of the sealer assembly.
Figure 25:
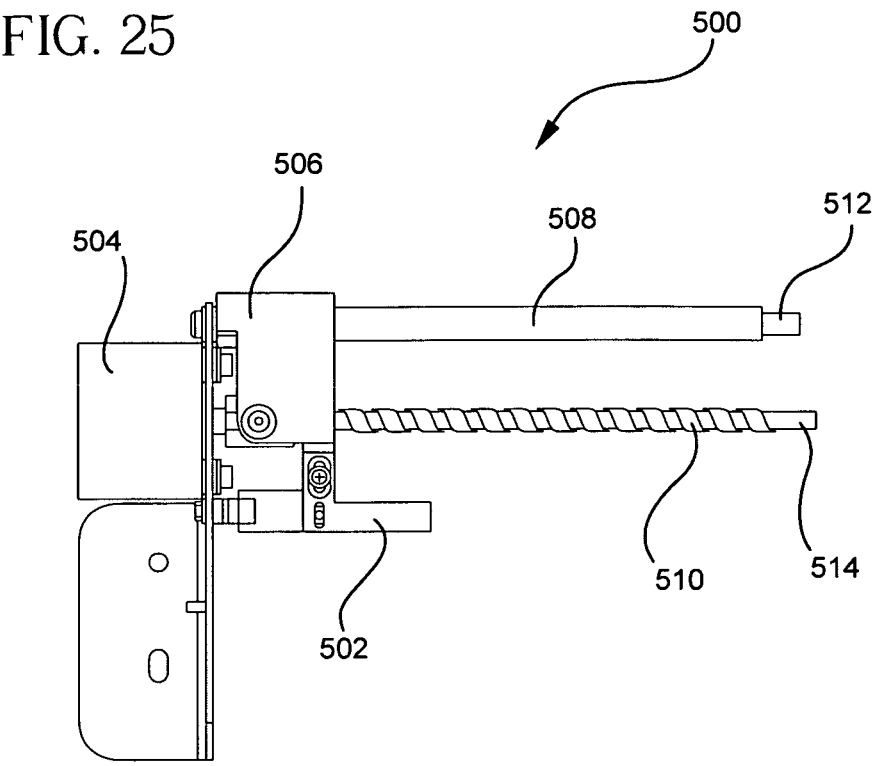
FIG. 25 is a side view of the card autoloader subassembly.
Figure 26:
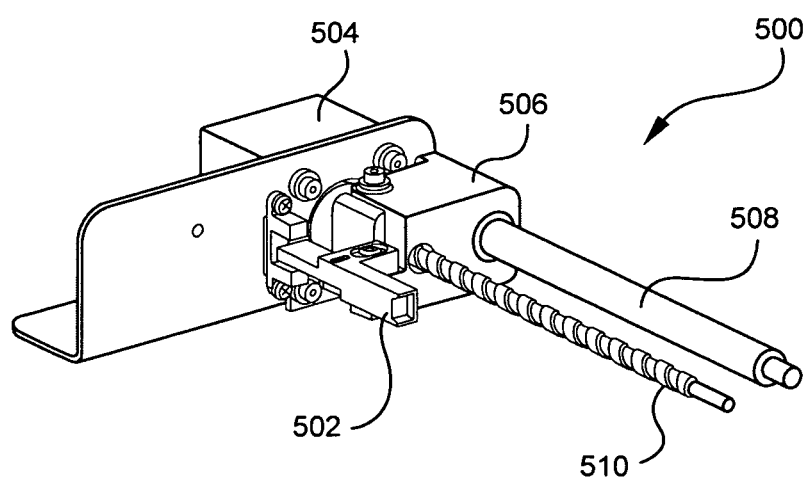
FIG. 26 is a perspective view of the card autoloader subassembly of FIG. 25.

Card Transport System 700 (FIGS. 16, 17 and 20)

As best shown in FIGS. 16, 17 and 20, the instrument includes a card transport system 700 that transfers the cards from the incubation station 600 past the optical reading station 800 for reading of the wells 104 in the cards 100. The card transport system 700 is essentially the same as described in the prior U.S. Pat. Nos. 5,798,085; 5,853,666; and 5,888,455, which are incorporated by reference herein. Accordingly, a more detailed description is omitted for the sake of brevity. Basically, the card is held in a vertical attitude between a belt 704 and a ledge 702 and moved from right to left and left to right by means of a motor driving the belt 704 back and forth. The ledge includes a slot feature for holding cards in the vertical position as the belt drives the cards back and forth. As the cards are moved past the transmittance optics heads, the cards are moved in a precise fashion as explained below to obtain transmittance measurements for each of the wells in the card at a multitude of positions across the width of the wells. The card includes built-in alignment sensor stop holes 130 (FIG. 6) to accurately position the wells in the optical system.

Reading Station 800 (FIGS. 4, 5, 16 and 17)

Once the cards are placed in the card transport system 700, they are moved past the reading station 800. The reading station includes two transmittance optics modules 802 (see FIGS. 16 and 17) that are oriented vertically, in the same direction as the columns of wells in the card. Each module 802 obtains measurements from one column of wells. Together, the modules 802 obtain transmittance measurements of the wells of the card in two columns of wells at the same time. The construction and manner of operation of the optical reader station 800 is essentially the same as described in the prior U.S. Pat. Nos. 5,798,085; 5,853,666; and 5,888, 455, therefore only a general overview and discussion will be set forth herein for sake of brevity. Unlike these patents, the illustrated embodiment provides only transmittance measurements, but of course fluorescence measurements could be taken as described in these patents by either replacing one of the modules 802 with a fluorescence module (see U.S. Pat. No. 5,925,884) or adding a fluorescence module to provide three modules. Additional modules of course could be provided.

The card 100 is positioned and read by the transmittance optical system modules 802 and returned to the carousel slot from which it was ejected. No data analysis takes place in the instrument; optical data is collected and transmitted to a remote workstation for analysis. Raw data may be queued and transmitted to the workstation later, in the event that communications between the instrument and workstation is not occurring.

The reader station 800 scans each of the cards 100 once every fifteen minutes, for four scans per hour. Each time the card is read, it returns to the carousel to be incubated until the next reading cycle. After the last reading cycle is complete, the card is transported through the optics to the card disposal system 900 for card ejection into the waste collection container.

The reader system 800 and card transport system 700 together performs card positioning and optical data collection in order to periodically monitor the growth of organisms inside the wells of the test cards. Optical transmittance data is used to quantify organism growth by measuring the optical transmittance of each well versus time. The illustrated embodiment currently supports two types of optics modules 802. The first module 802 has 660 nm LEDs illumination sources for each well. The other module 802 has 428 nm and 568 nm LEDs for each well. Development of a third module with additional wavelengths is of course possible.

Each optics module 802 has 8 measurement LEDs so that it can read 8 sample wells per column. Each card has 8 (or 16) columns of wells for a total of 64 wells per card. Each module 802 includes not only the transmittance LED light source for each well but also a detector for each well that captures the LED light after passing through the well. The detectors use silicon photodiodes. Sampling takes place as the card, with its 8 columns of 8 sample wells, moves through the optical path (from LED to photodiode) of the modules 802. The reading system scans across each well as the card is moved by the transport system 700 in 16 spatially separated steps, taking 3 readings per step. This data is then processed to reduce the effect of any bubbles that may have formed in the wells. The readings are smoothed and the peak value is chosen.

The emitter and detector housings in the modules 802 are hinged for ease of servicing and access to the optics area for cleaning. This detection system is capable of auto calibrating internally through air for 30% to 100% transmission (no light to full light). The optics is calibrated to 100% transmission through air automatically before reading each card.

Disposal System 900 (FIGS. 16, 17, 20)

Once incubation and optical testing of a test sample card 100 is complete, the card is automatically removed from the carousel in the incubation station 600, passed through the reader station 800, and transferred to a disposal system 900. The disposal system includes a disposal enclosure 904 that holds a waste container or bucket 906, and a ramp 908 that directs the card from the edge of the card transport system 700 into a chute 910 positioned directly above the waste container 906. The waste container is removable from the instrument 10 and is accessed via the door 902 shown in FIG. 1. The card is transported to the ramp 908 simply by operating the belt in the transport system 700 to the left to carry the card past the edge of the left-hand ledge 702.

The waste collection station 900 is located below the vacuum station 300 at the front of the instrument 10. It houses a removable waste container 906 (see FIG. 16) and a sensor (not shown) to detect when the container is installed. The user is notified when the waste container 906 is full or jammed by means of the user interface 22. Software in the instrument tracks the number of cards added to the container after it has been emptied.

Carrier Transport system 1000 (FIGS. 29-33)

The instrument 10 includes a system 1000 for transporting the carrier 200 from the loading and unloading station 16 through the carrier and test device processing subsystem 50.

The transport system 1000 is shown isolated in FIGS. 29-33 in order to better illustrate the components of the system. Their interrelationship with the various modules in the instrument 10 will be appreciated from inspection of the remaining figures, e.g., FIGS. 17, 19 and 20, and from the following discussion.

Basically, the transport system 100 includes the carrier 200 and a transport subassembly 1002 that moves the carrier 200 back and forth. The transport subassembly 1002 includes a cassette-engaging member 1004 in the form of a block that that is adapted to engage the carrier in the manner described below. The transport subassembly 1002 is constructed and arranged such that it moves the block 1004 and the carrier 200 back and forth along a single longitudinal axis between the carrier loading and unloading station 16, the sealing station 400, and the incubation loading station 500.

Figure 29:
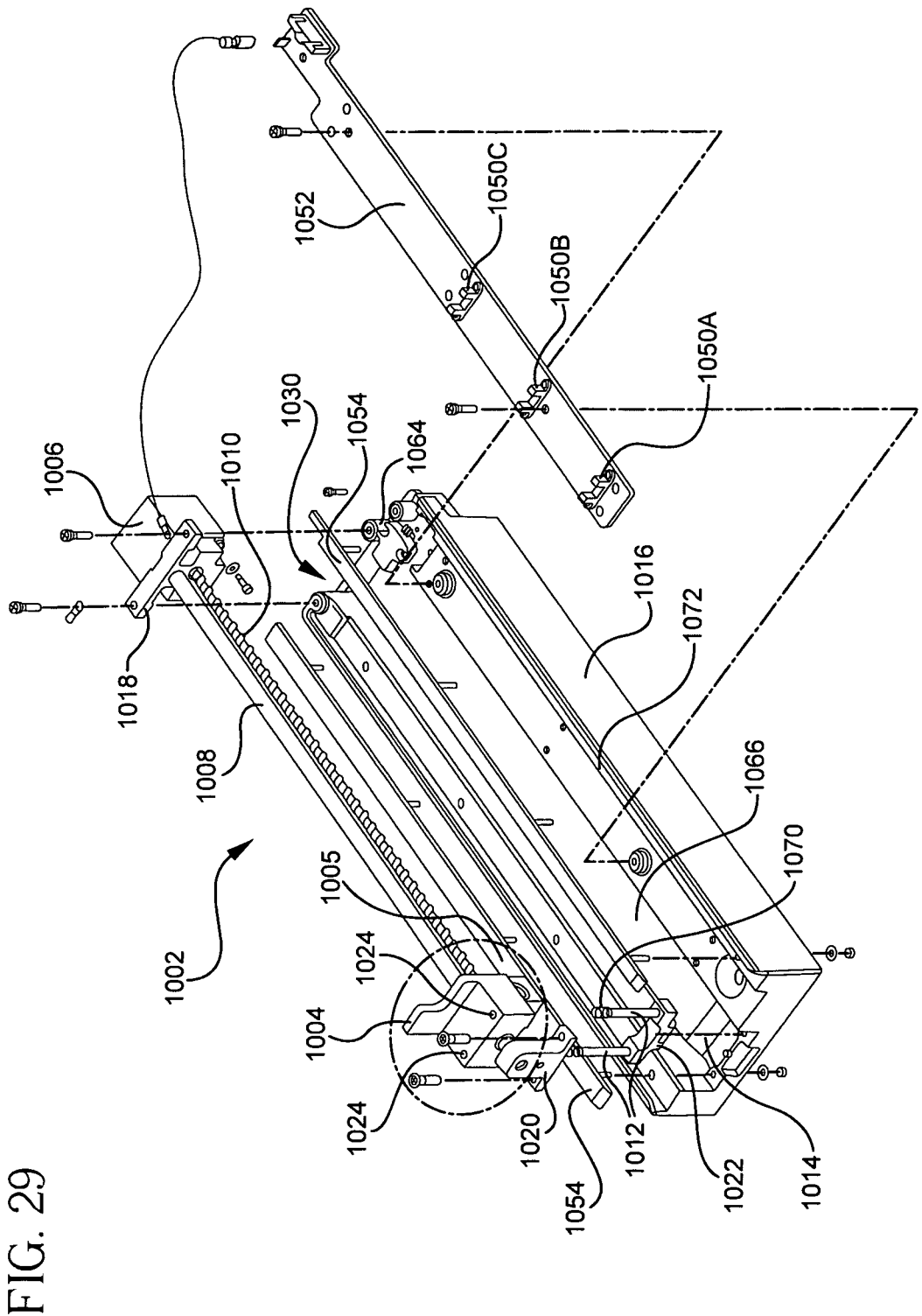
FIG. 29 is a perspective, exploded view of the transport assembly that moves the carrier of FIGS. 7-17 through the various modules or stations of the Carrier and Test Sample Device Processing Subsystem in the instrument of FIG. 1.
Figure 30:
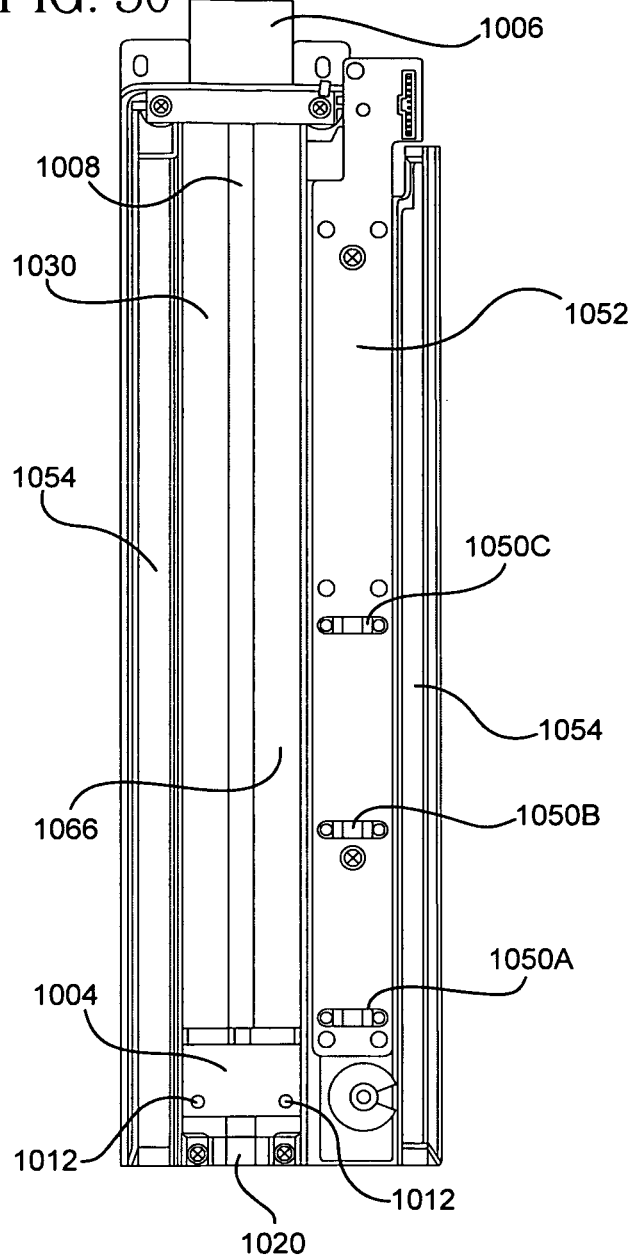
FIG. 30 is a top plan view of the transport assembly of FIG. 29.
Figure 31:
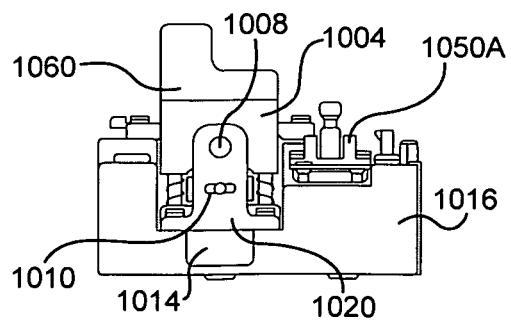
FIG. 31 is an end view of the transport assembly of FIGS. 29 and 30.
Figure 32:
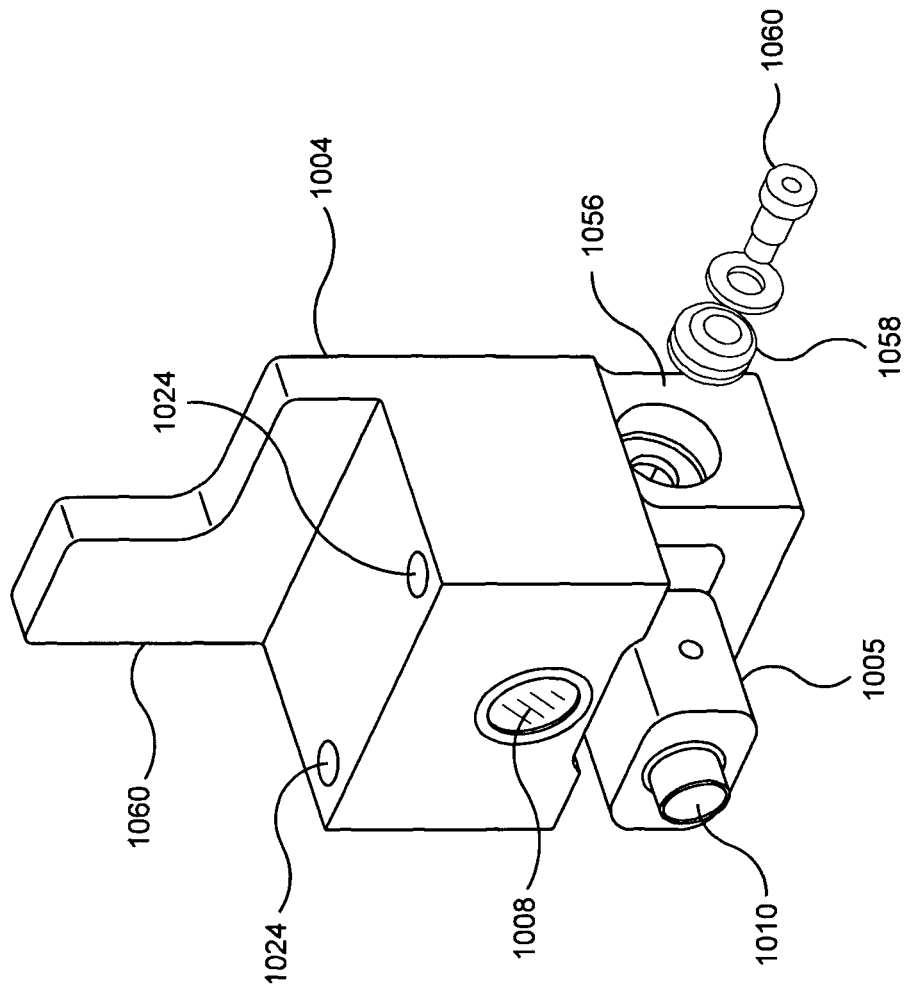
FIG. 32 is a detailed perspective view of the carrier-engaging block of FIG. 29-31.
Figure 33:
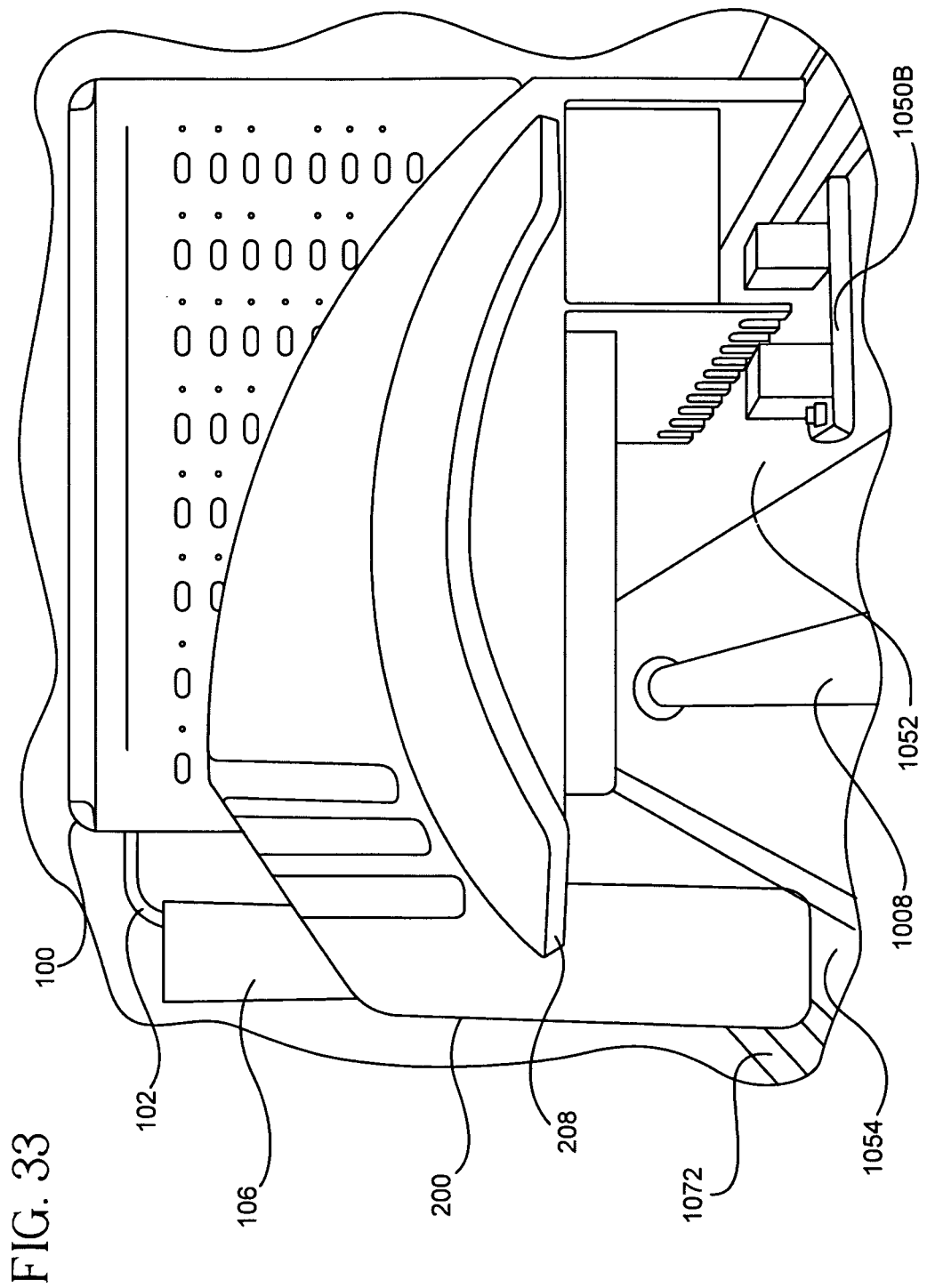
FIG. 33 is a view showing the movement of a loaded carrier past a detection station detecting the position of the carrier relative to a specific processing module in the instrument, here the card autoloader subassembly of FIGS. 25 and 26.

The transport subassembly 1002 includes a linear actuator motor 1006 that rotates a threaded shaft 1010. The threaded shaft 1010 is received in a threaded nut 1005 (FIG. 32) that is attached to the block 1004. A cylindrical guide member 1008 extends between a motor/guide rod mount 1018 and a front bearing mount 1020. The front bearing mount 1020 is fastened to the base 1016 of the transport subassembly 1002 as shown in FIG. 29. A pair of lift pins 1012 extend upwards from a drive nut engagement slide 1022 through apertures 1024 in the block 1004. The lift pins are biased by springs 1026 to a lower position, such that when the block 1004 is positioned at the loading/unloading station 14, the lower edge of the lift pins 1012 are in contact with a ramp or cam surface 1014 formed in the base 1016. When the block 1004 is moved by the motor 1006 towards the rear of the instrument, the lift pins ride up the ramp 1014 and thereby extend through the apertures 1024. In this upper position, the lift pins can then make contact with features on the underneath side of the carrier 200 and thereby pull the carrier along the track 1030 as the motor 1006 moves the block 1004 towards the rear of the instrument to the bar code reading station 60.

In operation, a reflective sensor 1040 positioned on the side of the incubation station housing as shown in FIG. 17 detects the presence of a carrier in the loading and unloading station 16. As the linear actuator motor 1006 rotates the shaft 1010, the block 1004 is moved from the front of the instrument 10 and the two lift pins 1012 are lifted to engage the test sample carrier 200. The pins 1012 are lifted by means of the cam surface 1014 molded into the base 1016 of the transport subassembly 1002. The pins 1012 are attached to the drive nut engagement slide 1022, which holds ball bearing wheels (not shown). The ball bearings ride up the cam surface 1014, lifting the pins 1012, when the motor 1006 is indexed to move the block 1004 to the rear of the instrument. The carrier 200 is then dragged into the instrument past a second reflective sensor 1042 (also shown in FIG. 17), which counts the number of test sample cards and determines their location in the carrier. The carrier 200 and its test sample cards are then presented to the bar code reader station 60, which reads the bar codes on the test sample cards 100 and the carrier 200.

After the bar codes are read, the motor reverses and moves the carrier toward the front of the instrument towards the loading and unloading station 14. During the forward travel the hot wire in the sealing station 400 is deployed and the test sample cards are sealed. The motor 1006 reverses again and the carrier 200 is moved to the card autoloader station 500 and placed into position where the test sample cards can be pushed off the carrier 200 and into the incubation station 600.

Three optical interrupt sensors 1050A, 1050B and 1050C (FIGS. 29 and 30) track the position of the carrier 200 over the entire travel. The three sensors 1050 are mounted to a single printed circuit board 1052 that is snapped into the transport subassembly base 1016. The carrier 200 slides over removable and replaceable wear strips 1054. The wear strips 1054 minimize friction between the carrier 200 and the base 1016.

As noted above, the linear actuator stepper motor 1006 moves the block 1004. The block 1004 restrains the lift pins 1012. The motor's shaft 1010 extends nearly the entire length of the subassembly 1002. The end of the shaft 1010 rotates in a pillow block bearing 1020 shown best in FIG. 29. The motor end mounts into an aluminum bracket 1018. The motor 1006 is mounted to the bracket 1018 indirectly via four vibration control grommets and shoulder screws.

The rotating motor 1006 drives an acme threaded nut 1005 (FIG. 32) along the length of the shaft 1010. The nut 1005 is pressed into the aluminum block 1056, which is coupled indirectly to the drive block 1004 via two vibration control grommets 1058 and shoulder screws 1060. The shoulder screws 1060 allow the nut 1005 to self align, preventing the nut 1005 from binding with the shaft 1010. The grommets 1058 prevent noise generated by the nut 1005 from transmitting through the drive block 1004 and into the base 1016.

The drive block 1004 is moved horizontally by the nut 1005. When moving toward the front of the instrument, a bearing surface 1060 on the block 1004 pushes the rear surface 220 (FIG. 14) of the carrier 200. When moving toward the back of the instrument, the two lift pins 112 lift through the holes 1024 in the drive block to engage a rib 222 on the underside of the sample carrier (see FIG. 15).

When the drive block 1004 is at the front, the block functions as a stop for a new sample carrier 200 being inserted into the instrument. When the drive block 1004 is at the back of the instrument, a reflective sensor 1064 (FIG. 29) detects it and indicates to the instrument microcontroller that the block 1004 is in its home position.

Three optical interrupt sensors 1050A, 1050B and 1050C are mounted to the printed circuit board 1052. The use of the circuit board 1052 eliminates the wires screws required when mounting the sensors directly to the base 1016. The sensors 1050A, 1050B and 1050C detect the notches 212 on the underside of the carrier 200, as explained above. Each notch corresponds to the location of a test sample card. The sensors are located on the printed circuit board at the card counter reflective sensor position (sensor 1050A), the bar code reading position (sensor 1050B), and the incubator loading position (sensor 1050C). The sensors 1050A-C allow the carrier's position to be continuously monitored.

The lift pin subassembly consists of two vertical pins 1012 mounted into an aluminum block 1022 containing two ball bearing rollers (not shown) at the base of the pins, functioning as wheels. The horizontal surface 1066 the wheels roll on is stepped near the front of the instrument to provide the cam or ramp surface 1014. The step is angled to allow the wheels to roll up and down, raising and lowering the pins 1012. Compression springs 1070 on the pins between the drive block 1004 and the body of the lift pin subassembly ensure that lift pin subassembly drops when rolling down the cam 1014.

Rails 1072 are provided to constrain the carrier's motion to forward and backward. The wear strips 1054 are mounted on the left and right horizontal surfaces of the base 1016 as shown in FIG. 29 to provide a low friction and wear surface for the carrier 200 to slide on.

The front cover 602 of instrument incubator station 600 provides three functions for the transport system. Firstly, a horizontal rib 1080 (FIG. 17) prevents test sample cards from sliding off the right side of the carrier 200 prior to insertion into the incubation station 600. Secondly, the reflective sensor 1040 (also FIG. 17) mounted near the front determines when the carrier 200 is present in the loading station. Thirdly, the sensor 1042 mounted just behind the sensor 1040 counts the test sample cards 100 and determines their location on the carrier 200.

As best shown in FIGS. 3A and 16, the front panel of the instrument has a tapered entryway in the loading and unloading station 16 for loading for the carrier 200. The carrier 200 is inserted until it contacts the drive block 1014. The door 14 is closed and the sensor 1040 registers the carrier's presence. The space between the door 14 and drive block 1004 is such that the reflective sensor 1040 will always detect the carrier 200 if it is present in the loading and unloading station.

Control Electronics and Firmware

The instrument 10 includes control electronics and firmware for controlling the operation of the various modules and subsystems of the instrument. The control electronics is conventional. Such electronics and firmware can be developed with ordinary effort by persons skilled in the art from the present disclosure, given the present state of the art.

Figure 34:
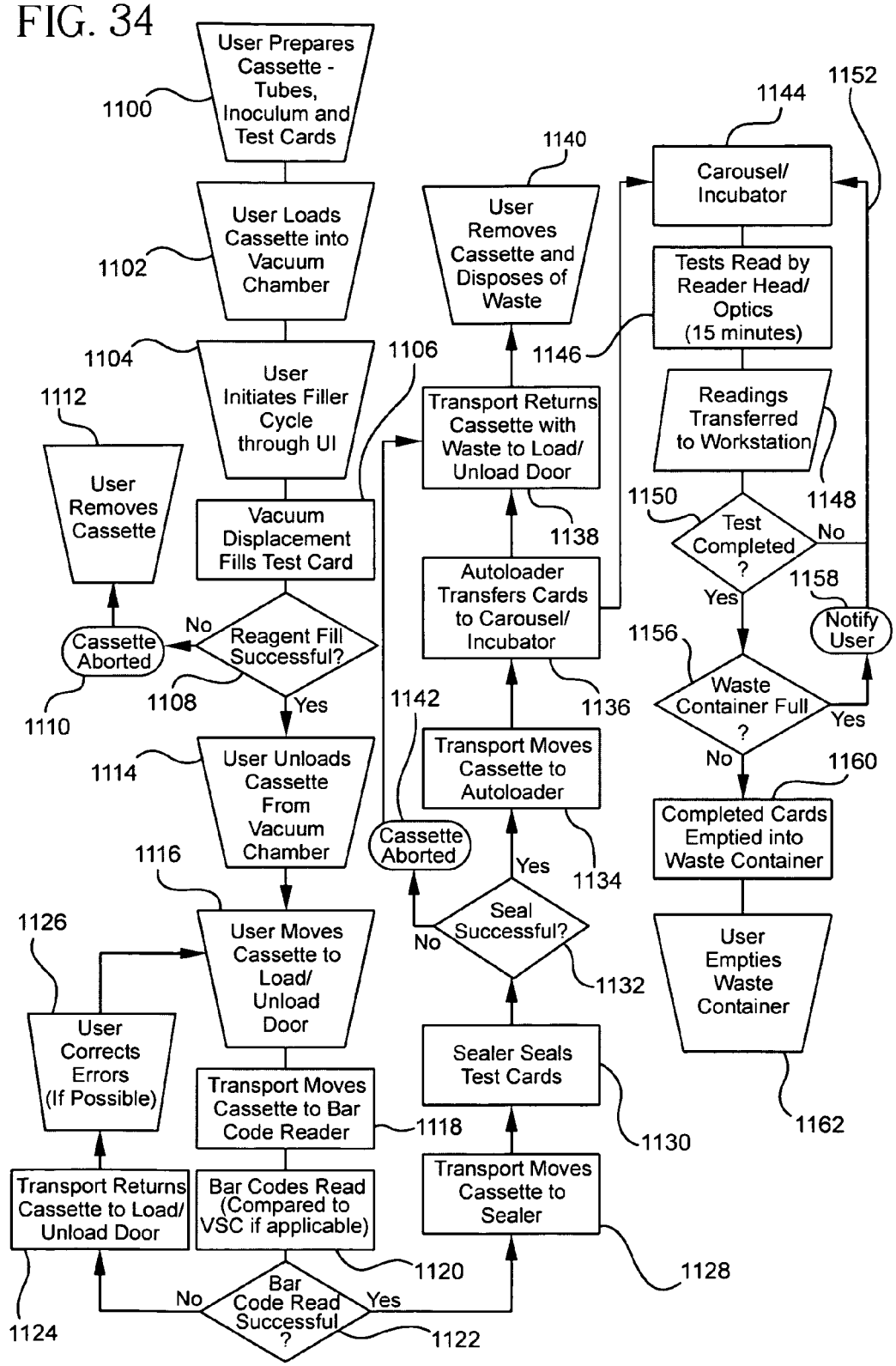
FIG. 34 is a detailed flow chart showing the workflow and sequence of steps in the use of the instrument and associated carrier, test sample receptacles and test sample devices.
Figure 35:
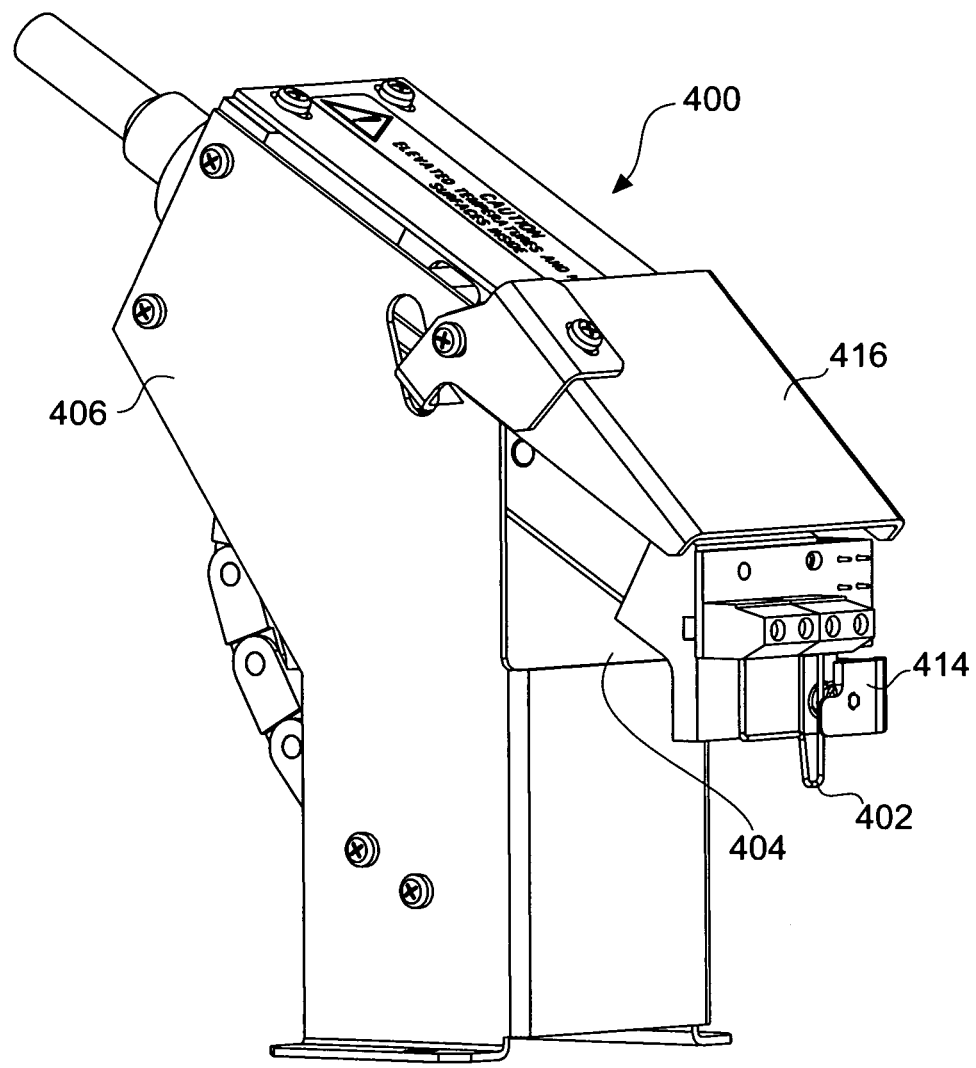
FIG. 35 is an assembled view of the sealer of FIG. 23.

Work Flow (FIG. 34)

The work flow and processing steps for the instrument 10 will now be described in conjunction with FIG. 34 together with the other Figures. At step 1100, the user prepares the sample inoculum off line, loads the fluid samples into the test tubes, scans the bar codes on the cards 100, and loads the cards 100 and test tubes into the carrier (cassette) 200. The bar code may be scanned off line with a separate bar code scanner. The scanning steps may be performed at a separate identification station having a workstation or computer programmed to receive information regarding the samples being tested, the scans of the bar codes on the cards being used, and the scan of the carrier bar code.

At step 1102, the user opens the vacuum chamber door 302 and loads the loaded carrier (as in FIG. 7) into the vacuum chamber 304, see FIG. 3A. The user then closes the door 302 to thereby seal the chamber.

At step 1104, the user initiates the vacuum cycle filling the cards via the user interface 22 keypad.

At step 1106, the vacuum pump is energized and a vacuum is generated inside the vacuum chamber 304. The vacuum displacement fills the cards in the carrier in the manner described above.

At step 1108, a test is made to see if the reagent fill was successful. The vacuum slope and time are monitored to insurer reagent fill.

At step 1110, if the reagent fill was not successful, the carrier processing is aborted as indicated at step 1112 and the user removes the carrier 200 the vacuum station 300.

At step 1114, if the reagent fill was successful, the user unloads the carrier 200 from the vacuum chamber 304.

At step 1116, the user opens the door 14 and manually places the carrier into the loading and unloading station 16. The detection of the carrier is made by the sensor 1040 (FIG. 17).

At step 1118, the transport system 1000 moves the carrier 200 to the bar code reader station 60. En route, the cards 1000 loaded into the carrier are detected by the card sensor 1042 (FIG. 17).

At step 1120, the bar codes in the carrier and on the cards are read by the bar code scanner in the reader station 60. The bar codes for the carrier and the cards are compared to the bar codes scanned off-line (if such scanning was done).

At step 1122, the instrument determines whether the bar code read was successful. If not, the process proceeds to step 1124 where the transport system 1000 moves the carrier back to the loading/unloading station 16 and the door 14 is unlocked. At step 1126, the user corrects errors if possible.

If the bar code read was successful, the process proceeds to step 1128. At this step, the transport system moves the carrier to the sealer station 400.

At step 1130, the sealer station 400 operates to seal each of the test sample cards in the carrier in the manner described above. The transfer tube remnants fall into the test tubes. The remaining stub seals the test sample cards.

At step 1132, a check is made to determine whether the seal of all the cards was successful. This is done by monitoring the hot sealer wire current, monitoring the sealer motor steps, and monitor the transport motor steps, and if there are no errors, the sealer worked.

If the sealing step was not successful, the process proceeds to step 1142 and the test is aborted and the processing proceeds to step 1138.

If the sealing step was successful, the transport system 1000 moves the carrier 200 to the card autoloader system 500, as indicated at step 1134. The card autoloader is described previously.

At step 1136, the card autoloader station 500 operates to load the cards one at a time into the carousel in the incubation station 600. The incubator carousel may rotate or index to any available position to accommodate the next card.

At step 1138, after step 1136 is completed, the transport system 1000 moves the carrier 200 with the test tubes and transfer tube remnants to the loading and unloading station 16.

At step 1140, the user removes the carrier 200 and disposes of the test tubes and their contents. The carrier is now ready for reuse.

At step 1144, the cards 100 are now housed in the incubation station 600 where they are incubated at a constant temperature.

At step 1146, the cards are periodically pushed out of their slot in the carousel and placed into the card transport system 700, where they are shuttled back and forth to the reading system 800. The reading of all the wells in the card is designed to occur at every 15 minutes.

At step 1148, the transmittance measurements obtained by the optics modules 802 are transmitted to the separate workstation via communications ports or interfaces in the instrument 10.

At step 1150, a check is made to determine if the reading of the cards is complete. This would occur such as by whether a reaction has occurred in one or more of the wells such that the periodic reading of the cards indicates that identification of the sample or susceptibility of the sample can be determined. If the test is not complete (i.e., more reading needs to occur), the processing proceeds to path 1152 and the card is sent back to its slot in the carousel for more incubation and additional reading, and steps 1144, 1146, 1148 and 1150 repeat.

If, at step 1150, the reading is complete, a check is made to see if the waste container in the disposal station enclosure 904 is full. If so, the user is notified at step 1158. If not, the card transport system 700 moves the card all the way to the left past the end of the ledge 702 and the card falls into the disposal system chute 910 and lands in the waste container in the enclosure 904.

At step 1162, the user periodically empties the waste container.

Variation from the specifics of the disclosed embodiments are to be expected depending on the configuration of the test devices and other factors. The scope of the invention is to be determined by reference to the appended claims, in view of the above.

We claim:

1. A sealer for cutting and sealing a conduit connecting a test sample device to a fluid receptacle containing a fluid sample, said sealer installed in an automated sample testing instrument, comprising an enclosure having an aperture:
   a moveable cutting element assembly having a home position within said enclosure and a deployed position outside said enclosure, said cutting element assembly comprising a cutting wire, a spring and a spring-loaded member biased by the spring adapted for engagement with said test sample device when said cutting element assembly is moved to said deployed position, and
   a motor for moving said cutting element assembly from said home position through said aperture in said enclosure to said deployed position;
   control electronics operably connected to the motor and to at least one sensor and configured for governing the operation of the motor; so that,
   when said cutting element assembly is moved to said deployed position, the engagement of said spring-loaded member with said test sample device urges said test sample device against a fixed structure in said instrument to thereby hold said test sample device in a fixed position while said cutting wire cuts and seals said conduit.

2. The sealer of claim 1, further comprising a constant current source providing current to said cutting wire.

3. The sealer of claim 1, wherein said motor is oriented and arranged such that said motor drives said cutting element assembly relative to said enclosure for cutting said cutting element assembly in a direction having both vertical and horizontal components relative to said aperture in said enclosure, whereby adjustment of the operation of said motor results in adjustment of said cutting element assembly relative to said instrument in both horizontal and vertical directions.

4. A sealer for cutting and sealing a conduit connecting a test sample device to a fluid receptacle containing a fluid sample, said sealer installed in an automated sample testing instrument, comprising an enclosure having an aperture:
   a moveable cutting element assembly having a home position within said enclosure and a deployed position outside said enclosure, said cutting element assembly further comprising a cutting wire cutting and sealing said conduit when said cutting element assembly is moved to said deployed position, and
   a motor for moving said cutting element assembly from said home position through said aperture in said enclosure to said deployed position;
   control electronics operably connected to the motor and to at least one sensor and configured for governing the operation of the motor; so that
   said motor is oriented and arranged such that said motor drives said cutting element assembly relative to an enclosure for said cutting element assembly in a direction having both vertical and horizontal components relative to said aperture in said enclosure, whereby adjustment of the operation of said motor results in adjustment of said cutting element assembly relative to said instrument in both horizontal and vertical directions.

5. The sealer of claim 4, wherein said motor moves said sealer along a line in a vertical plane relative to said instrument, and wherein said line is inclined relative to a horizontal axis by an angle of between 20 and 70 degrees.

6. The sealer of claim 1, wherein said test sample device comprises a multi-well test sample card and wherein said conduit comprises a transfer tube for introduction of a fluid sample into said test sample card.

7. The sealer of claim 4, wherein said test sample device comprises a multi-well test sample card and wherein said conduit comprises a transfer tube for introduction of a fluid sample into said test sample card.

\* \* \* \* \*

UNITED STATES PATENT AND TRADEMARK OFFICE
CERTIFICATE OF CORRECTION

| | | |
|---|---|---|
| PATENT NO. | : 8,623,293 B2 | Page 1 of 1 |
| APPLICATION NO. | : 12/228782 | |
| DATED | : January 7, 2014 | |
| INVENTOR(S) | : Bishop et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1186 days.

Signed and Sealed this
Seventh Day of April, 2015

Michelle K. Lee
*Director of the United States Patent and Trademark Office*